United States Patent
Tachas et al.

(10) Patent No.: US 8,765,700 B2
(45) Date of Patent: Jul. 1, 2014

(54) TOPICAL ADMINISTRATIONS OF ANTISENSE COMPOUNDS TO VLA-4 FOR THE TREATMENT OF RESPIRATORY CONDITIONS

(75) Inventors: George Tachas, Kew (AU); James G. Karras, San Marcos, CA (US); Susan Gregory, San Diego, CA (US); Jeffrey R. Crosby, Murrieta, CA (US); Kenneth W. Dobie, Del Mar, CA (US); Frank C. Bennett, Carlsbad, CA (US)

(73) Assignee: Antisense Therapeutics Ltd. (AU)

( * ) Notice: Subject to any disclaimer, the term of this patent is extended or adjusted under 35 U.S.C. 154(b) by 1168 days.

(21) Appl. No.: 11/666,001

(22) PCT Filed: Oct. 20, 2005

(86) PCT No.: PCT/AU2005/001634
§ 371 (c)(1),
(2), (4) Date: Jan. 7, 2008

(87) PCT Pub. No.: WO2006/086821
PCT Pub. Date: Aug. 24, 2006

(65) Prior Publication Data
US 2009/0029931 A1 Jan. 29, 2009

Related U.S. Application Data

(60) Provisional application No. 60/620,792, filed on Oct. 20, 2004, provisional application No. 60/648,820, filed on Jan. 31, 2005.

(51) Int. Cl.
*C12N 15/11* (2006.01)
(52) U.S. Cl.
USPC .................................................. 514/44 A
(58) Field of Classification Search
USPC ........................................... 514/44 A
See application file for complete search history.

(56) References Cited

U.S. PATENT DOCUMENTS

| 5,968,826 A | 10/1999 | Bennett et al. | |
|---|---|---|---|
| 6,258,790 B1 * | 7/2001 | Bennett et al. | 514/44 A |
| 2007/0161593 A1 * | 7/2007 | Karras et al. | 514/44 |

FOREIGN PATENT DOCUMENTS

| WO | WO 00/39292 A | 7/2000 |
|---|---|---|
| WO | WO 00/62736 A | 10/2000 |

OTHER PUBLICATIONS

European Search Report for Application No. 05857292.6, (Nov. 2005).
Georas et al. (2005) "T-helper cell type-2 regulation in allergic disease." *Eur Respir. J* 26: 1119-1137.
Examination Report issued Jul. 30, 2008 for New Zealand application NZ 554277.
Examination Report issued Apr. 29, 2009 for Australian application AU 2005327506.
Examination Report issued Jul. 2, 2009 for Australian application AU 2005327506.
Examination Report issued Jan. 28, 2010 for New Zealand application NZ 554277.
Examination Report issued Jun. 11, 2010 for European application EP 05 857 292.
Examination Report issued Apr. 15, 2011 for European application EP 05 857 292.
Translation of an Examination Report issued May 13, 2011 for Japanese application JP 2007-537071, and.
Translation of a Decision of Rejection issued Sep. 30, 2011 for Japanese application JP 2007-537071.

* cited by examiner

*Primary Examiner* — J. E. Angell
(74) *Attorney, Agent, or Firm* — Quine Intellectual Property Law Group P.C.

(57) ABSTRACT

A method for the treatment and/or prophylaxis of an animal having a respiratory disease or condition associated with airway hyperresponsiveness, eosinophilia, neutrophilia, leukocytes or overproduction of mucus and/or with the expression of integrin α4 comprising administering to the animal a composition comprising from. 0.001 to 1000 μg per kg body weight of the animal of an antisense compound targeted to a nucleic acid molecule encoding integrin α4.

14 Claims, 11 Drawing Sheets

TOPICAL ADMINISTRATIONS OF ANTISENSE COMPOUNDS TO VLA-4 FOR THE TREATMENT OF RESPIRATORY CONDITIONS

FIELD OF THE INVENTION

The present invention provides compositions and methods for treating respiratory conditions. In particular, this invention relates to oligonucleotide compounds, particularly antisense, which specifically hybridize with nucleic acids encoding human integrin α4.

BACKGROUND OF THE INVENTION

Inflammation is a localized protective response elicited by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. The adhesion of these leukocytes, or white blood cells, to vascular endothelium is an obligate step in the migration out of the vasculature (Harlan, J. M., Blood 1985, 65, 513-525). This response is mediated by the interaction of adhesion molecules expressed on the cell surface of leukocytes and vascular endothelial cells.

Very late activating antigen-4 (also called VLA-4, α4β1 or CD49d/CD29) is an integrin expressed in the surface of lymphocytes, monocytes, macrophages, mast cells, basophils and eosinophils. It is a heterodimeric adhesion receptor which is composed of noncovalently linked α4 and β1 subunits and serves to mediate leukocyte adhesion to vascular cell adhesion molecule-1 (VCAM-1) which is expressed on cytokine-stimulated endothelial cells. This interaction between VCAM-1 and VLA-4 contributes to leukocyte extravasation in acute and chronic inflammatory conditions including multiple sclerosis (MS), rheumatoid arthritis, asthma, psoriasis and allergy.

The α4 integrin subunit can also heterodimerize with a β7 integrin chain to form integrin α4β7 which is known as a mucosal homing receptor because its primary ligand is the mucosal vascular adhesion molecule MadCAM-1. Integrin α4β7 identifies a subset of memory T cells with a tropism for the intestinal tract, whereas integrin α4 μl (VLA-4) is constitutively expressed on most mononuclear leukocytes, but not on circulating neutrophils. The interaction of VCAM-1 with VLA-4 suggests that VLA-4 is a potential therapeutic target for inflammatory diseases, including many respiratory conditions, including, for example, asthma and bronchitis (Kassner, P. D., et al, Adv. Exp. Med. Biol. 1992, 323, 163-170).

Asthma is an inflammatory disease associated with eosinophil infiltration into the lung. VLA-4 is expressed on eosinophils. Metzger, W. J. (Springer Semin. Immunopathol. 1995, 16, 467-478) used a rabbit model of asthma to demonstrate that both an anti-VLA-4 antibody and a CS-1 peptide could reduce eosinophil infiltration into the lung and reduce the development of asthma.

While steroids and other antiinflammatory drugs are effective in treating inflammatory diseases and conditions, long-term usage often leads to side effects such as increased risk of infection caused by impairment of phagocytic leukocyte migration and function. There is some concern that inhibition of the function of the β1 integrin chain may be associated with increased susceptibility to infections, as demonstrated by a β1 (also called CD18) monoclonal antibody in rabbits (Foster, C. A., 1996, J. Allergy Clin. Immunol., 98, 270-277). It is believed that selective inhibition of the α4 chain may be a more desirable approach. Inhibition of the α4 chain is believed likely to reduce levels of the VLA-4 heterodimer as well as the α4β7 heterodimer.

Potential therapeutic interventions targeting VLA-4 include monoclonal antibodies and peptide antagonists. Antibodies specific for VLA-4 have been effective in attenuating allergen-driven airway inflammation and hyperresponsiveness in several experimental models of asthma, including the mouse. Leger, O. J. P. et al. (Human Antibodies, 1997, 8, 3-16) describe a monoclonal antibody against VLA-4 that is in phase III clinical trials for multiple sclerosis. CS-1 peptide antagonists have been described by Jackson, D. Y., et al. (J. Med. Chem. 1997, 40, 3359-3369). Hayashi et al. (Cell Struct. Funct. 1991, 16, 241-249) have used a vector expressing RNA complementary to chicken integrin β1 to reduce integrin β1 expression, resulting in altered cell attachment and shape.

Antisense oligonucleotides ("ASOs") targeted to various integrins have been used as tools to dissect the functional interactions of integrins in complex settings. Lallier and Bronner-Fraser (Science, 1993, 259, 692-695) have used phosphorothioate oligonucleotides targeted to conserved and nonconserved regions of chick β1, human α4, rat α1 and human β5 integrins to determine the effects of these integrins on cell attachment. These same oligonucleotides were also injected into cranial neural crest migratory pathways in avian embryos, and it was demonstrated that those oligonucleotides that inhibited cell attachment in vitro also caused neural crest and/or neural tube abnormalities in vivo (Kit et al., Devel. Biol. 1996, 179, 91-101).

EP patent application 688 784 (Carolus et al.) discloses 3' derivatized oligonucleotide analogs, including one sequence targeted to the β1 subunit of VLA-4.

U.S. Pat. Nos. 5,968,826 and 6,258,790 (Bennett et al.) describes modulating integrin α4 expression through the use of antisense oligonucleotides targeted to nucleic acids encoding integrin α4. U.S. Pat. No. 5,968,826 discloses that such antisense oligonucleotides can be used to treat a large variety of inflammatory diseases associated with VLA-4 expression, including asthma. According to this document, in general, a dosage of from 0.01 μg to 100 g of antisense oligonucleotide per kg of body weight, which may be given once or more times daily, weekly, monthly or yearly, or even every 2 to 20 years, may be used to treat the inflammatory diseases. The range of dosages exemplified for the various inflammatory diseases is from 0.01 mg to 20 mg of antisense oligonucleotide per kg body weight. Example 30 describes the prophetic use of antisense oligonucleotides in a murine model for asthma in which mice are injected intravenously with 1 mg/kg to 5 mg/kg doses of antisense oligonucleotides to integrin α4.

SUMMARY OF THE INVENTION

We have now found that respiratory diseases and conditions associated with airway hyperresponsiveness, eosinophilia, neutrophilia, leukocytes or overproduction of mucus and/or with the expression of integrin. α4 can be successfully treated or prevented using very low doses of antisense compounds targeted to nucleic acids encoding integrin α4.

Thus, the invention provides a method for the treatment and/or prophylaxis of an animal having a respiratory disease or condition associated with airway hyperresponsiveness, eosinophilia, neutrophilia, leukocytes or overproduction of mucus and/or with the expression of integrin α4 comprising administering to the animal a composition comprising from 0.001 to 1000 μg per kg body weight of the animal of an antisense compound targeted to a nucleic acid molecule encoding integrin α4.

The invention further provides a method for the treatment and/or prophylaxis of an animal having a respiratory disease or condition associated with airway hyperresponsiveness, eosinophilia, neutrophilia, leukocytes or overproduction of mucus and/or with the expression of integrin α4 comprising administering to the animal a composition comprising an antisense compound targeted to a nucleic acid molecule encoding integrin α4 at a dosage level of from 0.001 to 1000 μg of the antisense compound per kg body weight of the animal.

The invention further provides for the use of an antisense compound targeted to a nucleic acid molecule encoding integrin α4 in the manufacture of a medicament for the treatment and/or prophylaxis of an animal having a respiratory disease or condition associated with airway hyperresponsiveness, eosinophilia, neutrophilia, leukocytes or overproduction of mucus and/or with the expression of integrin α4 in which the medicament is to be administered at a dosage level equating to from 0.001 to 1000 μg of the antisense compound per kg body weight of the animal.

The invention further provides for a composition comprising an antisense compound targeted to a nucleic acid molecule encoding integrin α4 for use in therapy, in which the antisense compound is dosed at a level of from 0.001 to 1000 μg of the antisense compound per kg body weight of the animal being treated.

The use of such low dosages provides significant benefits including significantly reducing the potential for unwanted side-effects and providing a considerable cost saving in terms of the cost of manufacture per unit dose. In addition, it allows for greater flexibility in the potential devices of administration.

Suitably, the antisense compound is dosed at a level of at least 0.005, preferably at least 0.01, more preferably at least 0.05, more preferably at least 0.1, more preferably at least 0.5, yet more preferably at least 1 and yet more preferably at least 2 μg per kg body weight of the individual animal. The antisense compound may be dosed a higher levels such as, for example, at least 5 μg per kg body weight of the individual animal.

Suitably, the antisense compound is dosed at a level of less than 1000, preferably less than 500, more preferably less than 200, more preferably less than 150, more preferably less than 100, more preferably less than 75, more preferably less than 50, more preferably less than 20 and yet more preferably less than 10 μg per kg body weight of the individual animal. The antisense compound may be dosed at lower levels such as, for example, less than 7, less than 5, less than 2 or less than 1 μg per kg body weight of the individual animal.

Suitably, the antisense compound is dosed at a level of no more than 1000, preferably no more than 500, more preferably no more than 200, more preferably no more than 150, more preferably no more than 100, more preferably no more than 75, more preferably no more than 50, more preferably no more than 20 and yet more preferably no more than 10 μg per kg body weight of the individual animal. The antisense compound may be dosed at lower levels such as, for example, no more than 7, no more than 5, no more than 2 or no more than 1 μg per kg body weight of the individual animal.

Furthermore, we have found that antisense compounds targeted to nucleic acids encoding integrin α4 are especially effective when delivered topically. The finding that topical administration is particularly effective is surprising given the pharmacokinetics of antisense and/or the predominant mechanism of action of integrin α4 to modulate adhesion and transmigration of white blood cells from the blood into organs.

Thus, the invention further provides a method for the treatment and/or prophylaxis of an animal having a respiratory disease or condition associated with airway hyperresponsiveness, eosinophilia, neutrophilia, leukocytes or overproduction of mucus and/or with the expression of integrin α4 comprising topically administering to the animal a composition comprising an antisense compound targeted to a nucleic acid molecule encoding integrin α4.

The invention further provides for the use of an antisense compound targeted to a nucleic acid molecule encoding integrin α4 in the manufacture of a medicament for the treatment and/or prophylaxis of an animal having a respiratory disease or condition associated with airway hyperresponsiveness, eosinophilia, neutrophilia, leukocytes or overproduction of mucus and/or with the expression of integrin α4 in which the medicament is to be administered topically.

The invention further provides for a composition comprising an antisense compound targeted to a nucleic acid molecule encoding integrin α4 for use in therapy or prophylaxis, in which the antisense compound is to be administered topically.

Any suitable method of topical administration to the respiratory system or airway may be used including via the mouth or nose. Topical administration may be to any part of the respiratory system comprising the nose, throat, larynx, trachea, bronchial tubes and the lungs or to airways including the mouth and sinuses. Inhalation or insufflation are particularly preferred. Preferred routes are pulmonary, intranasal and intratrachael administration.

Thus, the invention also provides a composition comprising an antisense compound targeted to a nucleic acid molecule encoding integrin α4 in a formulation suitable for inhalation or insufflation.

Furthermore, the invention provides a composition comprising an antisense compound targeted to a nucleic acid molecule encoding integrin α4 in a formulation suitable for intranasal, intrapulmonary or intratracheal administration.

Preferably the composition containing the antisense compound is powdered or aerosolised and inhaled by the individual. Suitably, the composition is administered through a metered dose inhaler (MDI), nebuliser, dry powder inhaler (DPI), nasal inhaler or as nasal drops. This offers significant advantages in terms of ease and simplicity of use. Choice of device also enables delivery to different parts of the respiratory system. Nasal drops or nasal inhalers are often used to deliver to the upper respiratory tract such as the nose for treatment of nasal conditions such as rhinitis, whereas MDI and DPI are often used to deliver to the lower respiratory tract for treatment of conditions such as asthma.

The ability of low doses of oligonucleotides to work when administered topically suggests that there is one or more mechanisms being effected at a predominantly topical, local level. Although not wanting to be bound by mechanism, it is proposed that the predominant mechanism of action of integrin α4 is to modulate adhesion and transmigration of white blood cells from the blood into organs. An intravenous, intraperitoneal, or subcutaneous route for delivery of the antisense drug to integrin α4 to white blood cells will predominantly interfere with the adhesion of α4 positive white blood cells to vascular endothelium to thereby interfere with the obligate step of migration of the integrin α4 positive white blood cells out of the vasculature to the respiratory system, the lung being the site of asthma. The use of a pulmonary route provides significant benefits including improved specificity for the integrin α4 expressed in lung or significant reduction of the potential for unwanted systemic side-effects involved in modulating integrin α4 in white blood cells which are involved in the normal surveillance of organs other than the lung such as the brain, knee, and skin. Clearly, the ability to achieve a local effect is highly beneficial, systemic responses having the potential to produce unwanted side-effects.

Previous integrin α4 inhibitors described in the prior art have typically relied on dosing regimes requiring more than one dose being administered daily. In addition, they have typically relied on dosage units considerably higher than those of the present invention. For example, Koo G. C. et al. (Am. J. Respiratory Crit. Care Med, Vol. 167, pp 1400-1409, 2003) dosed twice daily with a topical composition and reported that occupancy was good when dosing at 1 and 3 mg/kg.

We have found that the present invention can provide effective treatment of respiratory diseases or conditions when dosed once a day and even once every two days. This is significant because research indicates that there is a poor compliance rate (about 30-70%) in the case of drugs, such as corticosteroids, which have to be inhaled twice or more (maybe up to five times) daily.

Thus, the invention further provides a method for the treatment and/or prophylaxis of an animal having a respiratory disease or condition associated with airway hyperresponsiveness, eosinophilia, neutrophilia, leukocytes or overproduction of mucus and/or with the expression of integrin α4 comprising administering to the animal a composition comprising an antisense compound targeted to a nucleic acid molecule encoding integrin α4 no more than once daily.

The invention further provides for the use of an antisense compound targeted to a nucleic acid molecule encoding integrin α4 in the manufacture of a medicament for the treatment and/or prophylaxis of an animal having a respiratory disease or condition associated with airway hyperresponsiveness, eosinophilia, neutrophilia, leukocytes or overproduction of mucus and/or with the expression of integrin α4 in which the medicament is to be administered no more than once daily.

The invention further provides a composition comprising an antisense compound targeted to a nucleic acid molecule encoding integrin α4 for use in therapy or prophylaxis, in which the antisense compound is to be administered no more than once daily.

The invention further provides a kit comprising a composition comprising an antisense compound targeted to a nucleic acid molecule encoding integrin α4 and a device which allows the composition to be administered by inhalation or insufflation at a dosage level of from 0.001 to 1000 µg of the antisense compound per kg body weight of the animal.

The invention further provides a kit comprising a composition comprising an antisense compound targeted to a nucleic acid molecule encoding integrin α4 and instructions that the composition is to be administered at a dosage range of from 0.001 to 1000 µg of the antisense compound per kg body weight of the animal being treated, optionally with instructions that the composition is to be administered by inhalation or insufflation and/or no more than once a day.

The present invention also provides antisense compounds, particularly oligunucleotides, which are targeted to a nucleic acid encoding integrin α4. Thus, the invention further provides antisense compounds targeted to a nucleic acid molecule encoding integrin α4, wherein the antisense, compound is an antisense oligonucleotide comprising at least an 8 nucleobase portion of one of SEQ ID Nos 103 to 178. Preferably, the antisense oligonucleotide comprises at least a 10, more preferably at least a 13 and yet more preferably at least a 15 nucleobase portion from any one of SEQ ID Nos 103 to 178.

Without being limited by theory, it is believed that VLA-4 (α4β1) is involved in several pathophysiological processes underlying the disease asthma and other respiratory system conditions and α4β7 may also have a role in these conditions. The predominant mechanism of action of integrin α4 is to modulate adhesion and transmigration of white blood cells i.e leukocytes from the blood into organs such as the lung. The VLA-4 binds to VCAM on cytokine-stimulated endothelial cells which is important in the transmigration of the white blood cells, particularly eosinophils into lung and nasal passages. Once in the lung or nasal passage, the role of integrin α4 is less clear. VLA-4 activation and/or α4β7 may contribute to local inflammatory processes, bronchoconstriction, and mucus production, exacerbating symptoms by a number of potential mechanisms (see FIG. 10). Mast cells (α4β1/α4β1) and basophils (α4β1) release agents involved in bronchoconstriction and neutrophil activation and eosinophil activation (α4β1/α4β7) which lead to airway inflammation. Macrophages (α4 µl), B-cells (α4 µl), and T cells including Th2 positive leukocytes (α4β1/α4β7) together with eosinophils may also be involved in the airway inflammation as are airway epithelial cells (α4β1). Leukocytes are also believed to attach to local smooth muscle cell in the lung via VLA-4 which may contribute to bronchospasm. Finally, VLA-4 is involved in neovascularization and angiogenesis is important in lung remodelling which occurs in several diseases of the lung and nasal passage.

The methods and compositions of the present invention may be used to treat any respiratory disease or condition associated with airway hyperresponsiveness, eosinophilia, neutrophilia, leukocytes or overproduction of mucus and/or with the expression of integrin α4. Such diseases or conditions will be evident to the skilled person. Examples of respiratory conditions or diseases already know to be associated with an overproduction of mucus with can be treated by the methods and compositions of the present invention include, for example, chronic respiratory conditions like asthma, cystic fibrosis, alpha-1 antitrypsin deficiency, chronic obstructive pulmonary disease and chronic bronchitis. It will be understood that reference to respiratory herein includes the nose, throat, larynx, trachea, bronchial tubes and the lungs or to the passages filled with air such airways including the mouth and sinuses. and that the compositions of the invention can be used to treat diseases and conditions associated with any the aforementioned. For example, the compositions are potentially useful in treating conditions like rhinitis, where some of the effects of the disease manifest themselves in the upper respiratory tract, and in treating sinusitis and in treating diseases or conditions associated with leukocytes, neutrophils, eosinophilia or dependent on airway hyperresponsiveness (AHR).

It will be understood that, in relation to compositions, compounds, components, ingredients or the like described herein, any lower range limit described in relation to a particular composition, compound, component, ingredient or the like may be combined with any upper range limit described in relation to the same composition, compound, component, ingredient or the like to define a suitable range for that particular composition, compound, component, ingredient or the like.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

DETAILED DESCRIPTION OF THE INVENTION

Figure 1:
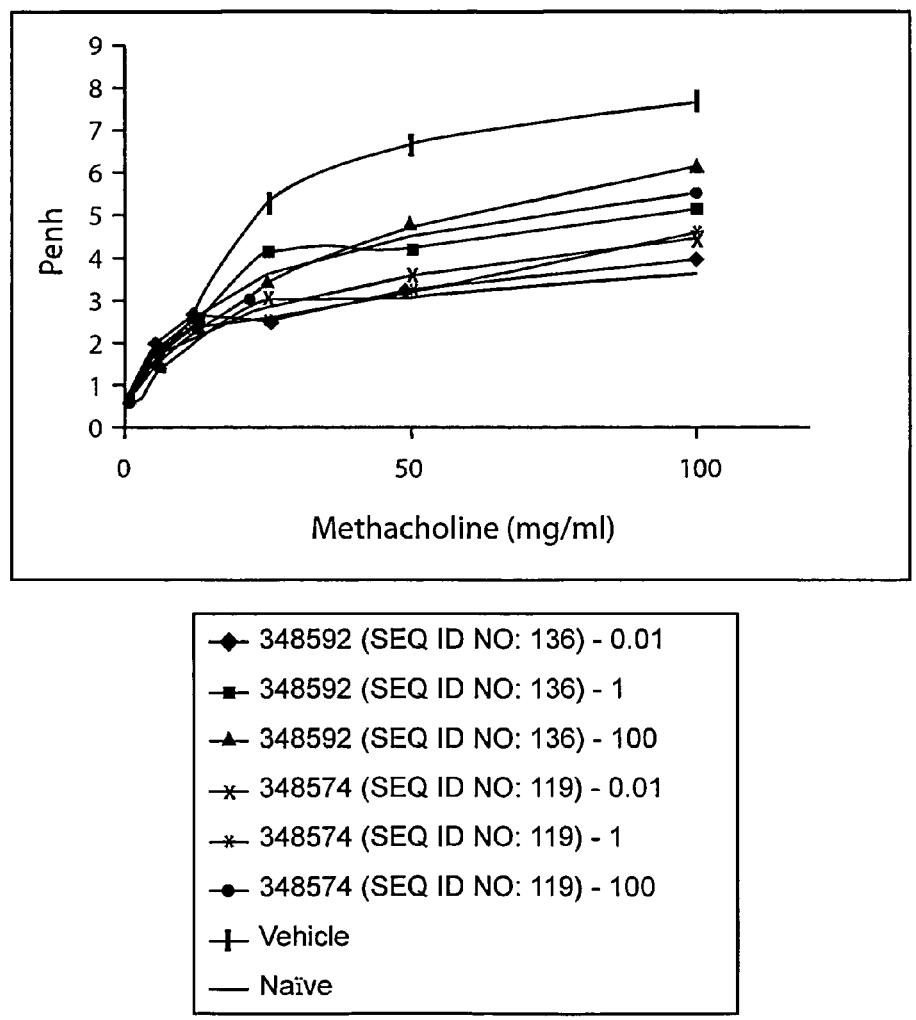
FIG. 1: Shows the effects of 0.0.1, 1 and 100 µg/kg doses of aerosolized integrin α4 ASOs (ISIS 348592 (SEQ ID NO: 136) or 348574 (SEQ ID NO: 119)) on Pen H at various doses of methacholine in an OVA model of asthma. The ASO treatment consisted of (1)—♦—is 348592 (SEQ ID NO: 136) at 0.01 µg/kg; (2)—■—is 348592 (SEQ ID NO: 136) at 1 µg/kg; (3)—▲—is 348592 (SEQ ID NO: 136) at 100 µg/kg; (4)—x—is 348574 (SEQ ID NO: 119) at 0.01 µg/kg; (5)—*—is 348574 (SEQ ID NO: 119) at 1 µg/kg; (6)—●—is 348574 (SEQ ID NO: 119) at 100 µg/kg; (7)—|—is the vehicle; (8)—is the naive.

The present invention employs oligomeric antisense compounds, preferably antisense oligonucleotides, for use in modulating the function of nucleic acid molecules encoding integrin α4, ultimately modulating the amount of integrin α4 produced. This is accomplished by providing antisense compounds which specifically hybridize with one or more nucleic acids encoding integrin α4. As used herein, the terms "target nucleic acid" and "nucleic acid encoding integrin α4" encompass DNA encoding integrin α4, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of integrin α4. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding integrin α4. The targeting process also includes determination of a site or sites within this gene for the antisense interaction to occur such that the desired effect, e.g., detection or modulation. of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon". refer to the codon or codons that are used in Vivo to initiate translation of an mRNA molecule transcribed from a gene encoding integrin $\alpha^4$, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region", which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary", as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. Reference herein to an oligonucleotide of a specified sequence and/or SEQ ID NO. therefore includes oligonucleotides composed of the naturally-occurring nucleobases, sugars and covalent internucleoside (backbone) linkages corresponding to the specified sequence and/or SEQ ID NO. as well as oligonucleotides having non-naturally-occurring portions which are based on the specified sequence and/or SEQ ID NO. and which function similarly. Suitable non-naturally occurring portions are described herein and will be evident to the skilled person and include modified or substituted oligonucleotides in which one or more of the nucleobases, sugars and/or covalent backbone linkages have been modified or substituted in some way.

The antisense compounds in accordance with this invention preferably comprise at least about 5, more preferably at least about 8, more preferably at least about 10, yet more preferably at least about 13 nucleobases, yet more preferably at least about 15 nucleobases and yet more preferably at least about 18 nucleobases. The antisense compounds preferably comprise up to about 50, more preferably up to about 40, more preferably up to about 30 nucleobases and yet more preferably up to about 25 nucleobases. Preferably, the antisense compounds in accordance with this invention comprise from about 8 to about 30 nucleobases, more preferably from about 10 to about 30 nucleobases and yet more preferably from about 15 to about 25 nucleobases. While antisense oligonucleotides are a preferred form of antisense compound, the present invention comprehends other oligomeric antisense compounds, including but not limited to oligonucleotide mimetics such as are described below. Particularly preferred are antisense oligonucleotides comprising from about 8 to about 30 nucleobases, more preferably from about 15 to about 25 nucleobases (i.e. from about 8 to about 30, more preferably from about 15 to about 25, linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, Cell, 1995, 81, 611-620). Montgomery et al. have shown that the primary interference effects of dsRNA are posttranscriptional (Montgomery et al., Proc. Natl. Acad. Sci. USA, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., Nature, 1998, 391, 806-811). Recently, it has been shown that it is, in fact, the single-stranded RNA oligomers of antisense polarity of the dsRNAs which are the potent inducers of RNAi (Tijsterman et al., Science, 2002, 295, 694-697). Single stranded and double stranded RNA (RNAi) inhibition of integrin α4 expression, and in particular human integrin α4 expression, is also within the scope of the present invention.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity in which the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl; backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., (Science, 1991, 254, 1497-1500).

Most preferred embodiments of the invention are oligonucleotides with phosphorothioate backbones and oligonucleosides with heteroatom backbones, and in —$CH_2$—NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$—[in which the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O—, S- or N-alkynyl; or O-alkyl-O-alkyl, in which the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in U.S. patent application Ser. No. 09/016,520, filed on Jan. 30, 1998, which is commonly owned with the instant application and the contents of which are herein incorporated by reference.

Other preferred modifications include 2'-methoxy (2'-O—$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference and allowed U.S. patent application Ser. No. 08/468,037, filed on Jun. 5, 1995, which is commonly owned with the instant application and is also herein incorporated by reference.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, Kroschwitz, J. I., ed. John Wiley & Sons, 1990, 858-859 those disclosed by Englisch et al., (Angewandte Chemie, IE, 1991, 30, 613), and those disclosed by Sanghvi, Y. S., (Antisense Research and Applications, 15, 289-302), and Crooke, S. T. and Lebleu, B., ed., (CRC Press, 1993). Certain of these nucleobases are particularly useful for increasing the binding affinity of the oligomeric compounds of the invention. These include 5-substituted pyrimidines, 6-azapyrimidines and N2, N-6 and O6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications 1993, 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res. 1992, 20, 533-538), an aliphatic chain, e.g., dodecandiol or undecyl residues (Saison-Behimoaras et al., EMBO J., 1991, 10, 1111-1118; Kabanov et. al., FEBS Lett., 1990, 59, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol. moiety (Crooke et al., J. Pharmacol. Exp. Ther., 1996, 277, 923-937.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras", in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region in which the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference, and allowed U.S. patent application Ser. No. 08/465,880, filed on Jun. 6, 1995, which is commonly owned with the instant application and also herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The present invention also provides novel antisense compounds, particularly oligonucleotides, which are targeted to a nucleic acid encoding integrin α4. In particular, the invention provides antisense compounds targeted to a nucleic acid molecule encoding integrin α4, wherein the antisense compound is an antisense oligonucleotide comprising at least an 8 nucleobase portion of one of SEQ ID Nos 103 to 178. Preferably, the antisense oligonucleotide comprises at least a 10, more preferably at least a 13 and yet more preferably at least a 15 nucleobase portion of one of SEQ ID Nos 103 to 178. In a preferred embodiment, the antisense oligonucleotide comprises one of SEQ ID Nos 103 to 178. Preferred antisense oligonucleotides are selected from SEQ ID NOs. 103, 104, 107, 110, 111, 112, 113, 114, 115, 116, 117, 118, 119, 120, 121, 122, 123, 124, 125, 126, 127, 128, 129, 130, 131, 132, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 171, 172, 173, 174, 177 and 178 or a portion thereof. Preferably, the antisense compound comprises an antisense oligonucleotide selected from the group consisting of SEQ ID NOs. 107, 110, 111, 112, 113, 114, 115, 116, 117, 118, 119, 120, 121, 122, 124, 126, 128, 130, 131, 132, 134, 135, 136, 137, 138, 141, 142, 143, 144, 145, 146, 147, 148, 149, 150, 151, 152, 153, 154, 155, 156, 157, 159, 160, 161, 163, 164, 165, 166, 167, 168, 169, 171, 172, 177 and 178 or a portion thereof. More preferably, the antisense compound comprises an antisense oligonucleotide selected from the group consisting of SEQ ID NOs. 111, 112, 113, 117, 119, 120, 121, 122, 130, 131, 132, 136, 138, 141, 144, 146, 147, 150, 151, 153, 154, 155, 156, 159, 160, 167, 169, 172 and 177 or portion thereof. Yet more preferably, the antisense compound comprises an antisense oligonucleotide selected from the group consisting of SEQ ID NOs. 117, 120, 121, 122, 128, 130, 131, 132, 136, 138, 141, 150, 159, 160, 167 and 169 or a portion thereof.

In addition to novel antisense oligonucleotides described, examples of other suitable antisense oligonucleotides and antisense oligonucleotide sequences for use in the compositions and methods of the present invention can be found in U.S. Pat. Nos. 5,968,826 are 6,258,790, the entire contents of which are herein incorporated by reference. In particular, the antisense oligonucleotides described in Tables 1, 2, 3, 5, 7, 10, 15 and 24 of the aforementioned US patents are potentially useful in the present invention. A particularly preferred antisense oligonucleotide from U.S. Pat. No. 6,258,790 is ISIS 107248 (CTGAGTCTGTTTTCCATTCT: SEQ ID NO: 81).

In a preferred embodiment, antisense compounds, and in particular antisense oligonucleotides, are targeted to a nucleic acid molecule encoding human integrin α4. This includes antisense compounds, and in particular antisense oligonucleotides, that cross-react with nucleic acid molecules encoding human integrin α4. Examples of preferred antisense oligonucleotides which cross react include antisense oligonucleotides selected from SEQ ID NOs. 117, 120, 121, 122, 128, 130, 131, 132, 136, 137, 138, 141, 149, 150, 159, 160, 161, 167, 168 and 81.

In a preferred embodiment, the antisense compound, and in particular an antisense oligonucleotide, inhibits the expression. of integrin α4, preferably human integrin α4, by at least 20, preferably at least 30, more preferably at least 40 and yet more preferably at least 50%.

Particularly preferred antisense oligonucleotide sequences are ISIS 348592 (GCAGCATATTTGTCACTTCC: SEQ ID NO: 136) and ISIS 107248 (CTGAGTCTGTTTTCCATTCT: SEQ ID NO: 81).

The compounds of the invention may also be admixed, encapsulated, conjugated or otherwise associated with other molecules, molecule structures or mixtures of compounds, as for example, liposomes and receptor targeted molecules for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al. J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts' include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized as therapeutics, prophylactics or palliatives. For therapeutics, an animal, preferably a human, suspected of having a disease, condition or disorder which can be treated by reducing airway hyperresponsiveness, eosinophilia, neutrophilia, leukocytes or overproduction of mucus and/or with the expression of integrin α4, preferably by modulating the expression of integrin α4, is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The methods and compositions of the present invention may be used to treat any respiratory disease or condition associated with airway hyperresponsiveness, eosinophilia, neutrophilia, leukocytes or overproduction of mucus and/or with the expression of integrin α4. Such diseases or conditions will be evident to the skilled person and include, for example, inflammatory, immune, mucus and angiogenic, airway hyperresponsive diseases or conditions. Examples of respiratory conditions or diseases associated with an overproduction of mucus with can be treated by the methods and compositions of the present invention include, for example, chronic respiratory conditions like asthma, cystic fibrosis, alpha-1 antitrypsin deficiency, chronic obstructive pulmonary disease and chronic bronchitis. The compositions may also be used to treat diseases or conditions more associated with the upper respiratory tract, such as the nasal passages and sinuses. For example, conditions like rhinitis, where some of the effects of the disease manifest themselves in the upper respiratory tract, and sinusitis may be treated. In addition, the compositions may be used to treat diseases or conditions associated with eosinophilia or dependent on airway hyperresponsiveness (AHR).

In one preferred embodiment, the antisence compounds targeting integrin α4 can be used to prevent, ameliorate and/or treat a condition or disease of the respiratory system or airways associated with airway hyperresponsiveness. For example the antisense can be used to prevent, ameliorate, and/or treat asthma.

In another embodiment, the antisence compounds targeting integrin α4 can be used to prevent, ameliorate and/or treat a condition or disease of the respiratory system and airways associated with allergic inflammation.

In another embodiment, the antisense compounds targeting integrin α4 can be used to prevent, ameliorate and/or treat a disease or condition of the respiratory system or airways associated with inflammatory cell infiltration. For example, the antisense compounds can be used to prevent, ameliorate and/or treat eosinophil infiltration, neutrophil and/or leukocyte infiltration.

In another preferred embodiment, the antisense compounds targeting integrin α4 can be used to prevent, ameliorate and/or treat a disease or condition of the respiratory system or airways associated with the overproduction of mucus.

The present invention also includes pharmaceutical compositions and formulations which include the antisense compounds of the invention. The pharmaceutical compositions of the present invention may be administered in a number of ways, although it is highly preferred that they be administered topically. Administration may be oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Medications for topical administration to the respiratory system or airway are generally taken orally or by inhalation. Preferably, the compositions of the invention are inhaled or insufflated using a suitable dosing device. The composition is preferably in powdered or aerosolised form. Suitable dosing devices will be evident to the skilled person and include, for example, metered dose inhalers (MDIs), nebulisers, dry powder inhalers (DPIs), nasal inhaler or as nasal drops. Conventional nasal spray devices may also be used. Choice of device depends on which part of the respiratory system delivery is desired. Nasal drops or nasal inhalers are often used to deliver to the upper respiratory tract such as the nose to treat nasal conditions such as rhinitis, whereas MDI and DPI are often used to deliver to the lower respiratory tract for conditions such as asthma.

Oral delivery may be predominantly for topical or systemic effects. Preferably, the compositions of the invention taken orally are for topical effects. Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Preferably, administration is topical to areas effected by the respiratory disease or condition. Suitably, administration is pulmonary, e.g., by inhalation or insufflation of powders or aerosols, including by nebulizer; intratracheal, intranasal, epidermal and transdermal.

Pharmaceutical compositions and/or formulations comprising the antisense compounds of the present invention may also include penetration enhancers in order to enhance the alimentary delivery of the antisense compounds. Penetration enhancers may be classified as belonging to one of five broad categories, i.e., fatty acids, bile salts, chelating agents, surfactants and non-surfactants (Lee et al., Critical Reviews in Therapeutic Drug Carrier Systems, 1991, 8, 91-192; Muranishi, Critical Reviews in Therapeutic Drug Carrier Systems, 1990, 7, 1-33). One or more penetration enhancers from one or more of these broad categories may be included. Penetration enhancers. are described in pending U.S. patent application Ser. No. 08/886,829, filed on Jul. 1, 1997, and pending U.S. patent application Ser. No. 08/961,469, filed on Oct. 31, 1997, both of which are commonly owned with the instant application and both of which are herein incorporated by reference.

Various fatty acids and their derivatives which act as penetration enhancers include, for example, oleic acid, lauric acid, capric. acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., Critical Reviews in Therapeutic Drug Carrier Systems, 1991, 8, 91-192; Muranishi, Critical Reviews in Therapeutic Drug Carrier Systems, 1990, 7, 1-33; El-Hariri et al., J. Pharm. Pharmacol., 1992, 44, 651-654). Examples of some presently preferred fatty acids are sodium caprate and sodium laurate, used singly or in combination at concentrations of 0.5 to 5%.

Preferred penetration enhancers are disclosed in pending U.S. patent application Ser. No. 08/886,829, filed on Jul. 1, 1997, which is commonly owned with the instant application and which is herein incorporated by reference.

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y. 1996, pages 934-935). Various natural bile salts, and their synthetic derivatives, act as penetration enhancers. Thus, the term "bile salt" includes any of the naturally occurring components of bile as well as any of their synthetic derivatives. Preferred bile salts are described in pending U.S. patent application Ser. No. 08/886,829, filed on Jul. 1, 1997, which is commonly owned with the instant application and which is herein incorporated by reference. A presently preferred bile salt is chenodeoxycholic acid (CDCA) (Sigma Chemical Company, St. Louis, Mo.), generally used at concentrations of 0.5 to 2%.

Complex formulations comprising one or more penetration enhancers may be used. For example, bile salts may be used in combination with fatty acids to make complex formulations. Preferred combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, 8, 92-192; Muranishi, Critical Reviews in Therapeutic Drug Carrier Systems, 1990, 7, 1-33; Buur et al., J. Control Rel., 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, 8, 92-191); and perfluorochernical emulsions, such as FC-43 (Takahashi et al., J. Pharm. Pharmacol., 1988, 40, 252-257).

Non-surfactants include, for example, unsaturated cyclic ureas, 1-alkyl- and 1-alkenylazacyclo-alkanone derivatives (Lee et al., Critical Reviews in Therapeutic Drug Carrier Systems, 1991, 8, 92-191); and non-steroidal anti-inflammatory agents such as diclofenac sodium, indomethacin and phenylbutazone (Yamashita et al., J. Pharm. Pharmacol., 1987, 39, 621-626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity. by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., Antisense Res. Dev., 1995, 5, 115-121; Takakura et al., Antisense & Nucl. Acid Drug Dev., 1996, 6, 177-183).

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., Current Op. Biotech., 1995, 6, 698-708).

Liposome preparation is described in pending U.S. patent application Ser. No. 08/961,469, filed on Oct. 31, 1997, which is commonly owned with the instant application and which is herein incorporated by reference.

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, The Merck Manual of Diagnosis and Therapy, 1987, Berkow et al., eds., Rahway, N.J., 1206-1228. Anti-inflammatory drugs, including but not limited to nonsteroidal anti-inflammatory drugs and corticosteroids, and antiviral drugs, including but not limited to ribivirin, vidarabine; acyclovir and ganciclovir, may also be combined in compositions of the invention. See, generally, The Merck Manual of Diagnosis and Therapy, 1987, Berkow et al., eds., Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ s found to be effective in in vitro and in vivo animal models.

Preferably the dosage is in the range from 0.005 to 200 µg, more preferably from 0.01 to 200 µg, more preferably from 0.1 to 5 µg, and yet more preferably for 0.5 to 1 µg per kg of body weight. Dosages may be given once or more daily, weekly, monthly or yearly, or even once every 2 to 20 years. Preferably, doses are given no more frequently than once daily, more preferably no more frequently that once every two days.

While the present invention has been described with specificity in accordance with certain of its preferred embodiments, the following. examples serve only to illustrate the invention and are not intended to limit the same.

EXAMPLES

The ability of integrin α4-specific antisense oligonucleotides (ASOs) to inhibit the allergic inflammatory response to antigen challenge in the mouse lung was assessed.

Screen of Oligonucleotides for Ability to Suppress Expression of Integrin α4 mRNA.

A series of antisense oligonucleotides targeted to integrin α4 were screened in mouse bEND cells for their ability to reduce integrin α4 RNA levels ("% inhibition"). The design, modification, synthesis and testing of antisense compounds is described in the prior art, for example, in U.S. Pat. No. 6,743,909, the entire contents of which are incorporated herein by reference.

Briefly, cells were transfected with Lipofectin. Oligonucleotide concentration was 30 nM. All compounds shown are 5-10-5 MOE gapmers (i.e. 2'-O-methoxyethyl sugars on the five contiguous nucleosides at either end of the molecule and 2'deoxy nucleosides on the 10 central nucleosides) w/phoshorothioate backbone and 5-methylcystosine for every C.

The primer/probe set used was RTS2137 (all are unmodified except for labels on probe)":

```
Forward: ISIS 348635
                                    (SEQ ID NO: 100)
GAAAGGTAAAAAGCTTGGCTCATACT (deoxy, diester
backbone)

Reverse: ISIS 348636
                                    (SEQ ID NO: 101)
TCTGAGAAGCCATCTGCATTGA Probe: ISIS 348637
                                    (SEQ ID NO: 102)
5'FAM-TGGAGCTTCTGTCTGCGCTGTGGA-TAMRA3'
```

The results are presented in Table 1

TABLE 1

Inhibition of integrin α4 RNA levels

| ISIS No. | Sequence | SEQ ID No | % inhibition | Species Oligo hits |
|---|---|---|---|---|
| 348558 | AGAGCTTCAGTGTTTTGCTT | 103 | 17.9 | Mouse |
| 348559 | TATATGTACATACACACAAG | 104 | 25.8 | Mouse |
| 348560 | AGTGGCACCCACCTCCTCTT | 105 | 5.0 | Mouse |
| 348561 | TCAACCTCACCTTAGCAACA | 106 | 0.4 | Mouse |
| 348562 | CTTGGGATGCAATTAAATGC | 107 | 42.7 | Mouse |
| 348563 | AAATGCTTACCCTTGAGAGG | 108 | 13.0 | Mouse |
| 348564 | TCATGCAATACTTGAAAAGA | 109 | 13.3 | Mouse |
| 348565 | GGCCACTGACCAGAGTTGCA | 110 | 43.8 | Mouse/Rat |

TABLE 1-continued

Inhibition of integrin α4 RNA levels

| ISIS No. | Sequence | SEQ ID No | % inhibition | Species Oligo hits |
| --- | --- | --- | --- | --- |
| 348566 | CCGCAGCCATGCGCTCTTGG | 111 | 65.4 | Mouse |
| 348567 | CGCTTCCGCAGCCATGCGCT | 112 | 61.1 | Mouse |
| 348568 | CACCTCGCTTCCGCAGCCAT | 113 | 53.8 | Mouse |
| 348569 | CCAGGTTGTAGGAGTGCCCG | 114 | 47.3 | Mouse/Rat |
| 348570 | AGTAGCCAAACAGCGTGCCG | 115 | 46.0 | Mouse/Rat |
| 348571 | GTGGCTGTGCAGCACCACCG | 116 | 40.0 | Mouse/Rat |
| 348572 | CCCAGCTGGAGCTGTTCGCA | 117 | 52.8 | Human/Mouse/Rat |
| 348573 | GGCTACCCAGCTGGAGCTGT | 118 | 31.3 | Human/Mouse |
| 348574 | ATATTTTTCCACCTGTGCCC | 119 | 60.3 | Mouse/Rat |
| 348575 | GCAAAATTTTCTCCAAATTT | 120 | 50.3 | Human/Mouse/Rat |
| 348576 | ATGATGCAAAATTTTCTCCA | 121 | 57.3 | Human/Mouse |
| 348578 | CCAGCTTGACATGATGCAAA | 122 | 56.2 | Human/Mouse |
| 348579 | ATATTCCAGCTTGACATGAT | 123 | 20.6 | Human/Mouse |
| 348580 | GCCCCCATCACAATTAAATC | 124 | 33.8 | Human/Mouse |
| 348581 | GTAGTTATATTGTAGACAAA | 125 | 29.2 | Human/Mouse |
| 348582 | ACTGAGTAGCCTAAGTAGCT | 126 | 39.4 | Mouse |
| 348583 | CTATCTGTTCGTGTTGAGGG | 127 | 21.2 | Mouse/Rat |
| 348584 | CCAAGCTTTTTACCTTTCAT | 128 | 71.0 | Human/Mouse/Rat |
| 348585 | CAGACAGAAGCTCCAAAGTA | 129 | 25.7 | Human/Mouse/Rat |
| 348586 | CCATCTGCATTGAGGTCCAC | 130 | 65.4 | Human/Mouse/Rat |
| 348587 | AGAAGCCATCTGCATTGAGG | 131 | 64.3 | Human/Mouse/Rat |
| 348588 | ATCTGAGAAGCCATCTGCAT | 132 | 62.5 | Human/Mouse/Rat |
| 348589 | CTGATGGTGCTCTGCATGGG | 133 | 13.7 | Human/Mouse |
| 348590 | CCATGCCAGAGTTGATGTAC | 134 | 45.2 | Mouse/Rat |
| 348591 | CATTTCAACCATCACAGCTC | 135 | 40.1 | Mouse/Rat |
| 348592 | GCAGCATATTTGTCACTTCC | 136 | 70.7 | Human/Mouse/Rat |
| 348593 | ATCTTGCAGCATATTTGTCA | 137 | 44.3 | Human/Mouse |
| 348594 | CCCAAATCTTGCAGCATATT | 138 | 52.9 | Human/Mouse |
| 348595 | TTGTCAATGTCGCCAAGATT | 139 | 21.1 | Human/Mouse/Rat |
| 348596 | CCATTGTAAATGTAGACAGC | 140 | 27.1 | Mouse/Rat |
| 348597 | GTCCTTCAATTCTCTGTGAG | 141 | 66.9 | Human/Mouse |
| 348598 | TCTGCATCAATTTGTCCTGA | 142 | 44.9 | Human/Mouse/Rat |
| 348599 | CATATCCATTGTTGTCTGCA | 143 | 46.8 | Mouse/Rat |
| 348600 | TCCTTAGCAACACTGCAGAA | 144 | 56.2 | Mouse/Rat |
| 348601 | GATGCTTCAACAATCACTAC | 145 | 44.5 | Mouse/Rat |
| 348602 | ATGGCTTAAAGATGCTTCAA | 146 | 55.5 | Mouse/Rat |

TABLE 1-continued

Inhibition of integrin α4 RNA levels

| ISIS No. | Sequence | SEQ ID No | % inhibition | Species Oligo hits |
|---|---|---|---|---|
| 348603 | TAGCCTGGGACCTCTTTGCC | 147 | 52.1 | Mouse/Rat |
| 348604 | CAAAACGATGTAGCCTGGGA | 148 | 44.9 | Mouse/Rat |
| 348605 | CCTGTAATCACGTCAGAAGT | 149 | 47.7 | Human/Mouse |
| 348606 | TGCTTCCTGTAATCACGTCA | 150 | 63.7 | Human/Mouse |
| 348607 | CCACTGCTTGAAACTCGTAT | 151 | 52.8 | Mouse/Rat |
| 348608 | GGTGTGTCCTACATTTCTCT | 152 | 43.0 | Mouse/Rat |
| 348609 | GTCTTTCCGCATGAATGCCT | 153 | 52.1 | Mouse/Rat |
| 348610 | CCAAGGTGGTATGTGGCCTC | 154 | 51.2 | Mouse/Rat |
| 348611 | CACATGATGCCCAAGGTGGT | 155 | 58.3 | Mouse/Rat |
| 348612 | GTTTGTGATCACATGATGC | 156 | 52.9 | Mouse/Rat |
| 348613 | CAAAACCTTGCAAAGTTTAT | 157 | 33.0 | Human/Mouse |
| 348614 | ACATCCAGGAGAAAGCTAAT | 158 | 20.2 | Human/Mouse |
| 348615 | AGCTCACATCCAGGAGAAAG | 159 | 59.7 | Human/Mouse |
| 348616 | GAGTGAGCTCACATCCAGGA | 160 | 54.4 | Human/Mouse |
| 348617 | CTGCTGAGTGAGCTCACATC | 161 | 48.7 | Human/Mouse |
| 348618 | GTTCACAAGCCCATGAACAG | 162 | 29.1 | Mouse |
| 348619 | TACACAAATGAAGTTGGGTT | 163 | 33.8 | Human/Mouse |
| 348620 | ATCCATACACAAATGAAGTT | 164 | 40.5 | Human/Mouse |
| 348621 | AGAATTTGGTACCATTATTT | 165 | 39.4 | Human/Mouse |
| 348622 | TCATGCAATACAGGAGTCTC | 166 | 34.2 | Mouse |
| 348623 | CGTTTGGGTCTTTGATGATG | 167 | 52.2 | Human/Mouse |
| 348624 | ATAAGTCCAAGTAGCAAGCT | 168 | 46.6 | Human/Mouse |
| 348625 | GTACAATAAGTCCAAGTAGC | 169 | 59.1 | Human/Mouse |
| 348626 | TCTTGTAGGATAGATTTGTA | 170 | 14.8 | Human/Mouse |
| 348627 | TAGAAGTCTTCAGTCATCAT | 171 | 42.3 | Mouse |
| 348628 | GATTCCCTGCACTAAGAG | 172 | 53.5 | Mouse |
| 348629 | AAGCCACCTTTGGGTAGCTT | 173 | 24.2 | Mouse |
| 348630 | GACGGTTGGCCAAAGAGAAG | 174 | 21.3 | Mouse |
| 348631 | CACGATGAGCCTCCTCTTCC | 175 | 0.5 | Mouse |
| 348632 | CACACATGCATGATTATATT | 176 | — | Mouse |
| 348633 | GCCCCAAAGGAGATGTGATA | 177 | 50.6 | Mouse |
| 348634 | CGAGGCGAGCATTTACCAGC | 178 | 37.7 | Mouse |

As indicated in Table 1, a number of the oligonucleotides were cross-species compounds that are perfectly homologous to rat and/or human integrin α4 as well as the mouse sequence. From Table 1, it is evident that many compounds inhibited integrin α4 RNA levels by 50% or more.

The following two non-overlapping integrin α4 antisense oligonucleotides were selected for further evaluation:

ISIS 348592 (GCAGCATATTTGTCACTTCC: SEQ ID NO: 136), a 5-10-5 MOE gapmer (i.e. 2'-O-methoxyethyl sugars on the five contiguous nucleosides at either end of the molecule and 2'deoxy nucleosides on the 10 central nucleosides) w/phoshorothioate backbone and 5-methylcystosine for every C that is fully complementary to human, mouse and rat integrin α4.

ISIS 348574 (ATATTTTTCCACCTGTGCCC: SEQ ID NO: 119), a 5-10-5 MOE gapmer w/phoshorothioate backbone and 5-methylcystosine for every C that is fully complementary to mouse and rat integrin α4.

An 8 base pair-mismatch oligonucleotide for ISIS 348574 was also run. This was ISIS 358342 (ACAGTGTACCTC-CTTTTCTC: SEQ ID NO: 179), a 5-10-5 MOE gapmer w/phoshorothioate backbone.

Example 1

In vivo Study on Ability of Aerosol Administered ASOs to Reduce the Level of Integrin α4 Protein Expressed in Allergen Challenged Mice Airway inflammation is observed in patients with allergic asthma. This study evaluated the efficacy of ISIS 348592 (SEQ ID NO: 136) and ISIS 348574 (SEQ ID NO: 136)in an in vivo murine model of allergic asthma. Models of ovalbumin-induced lung inflammation and airway hyperreactivity (AHR) are described in the prior art. For example, they are described in U.S. Pat. No. 6,136,603, the entire contents of which is incorporated herein by reference. A preferred model is that developed by Hessel et al. (*J. Immunol.* 1998, 160, 2998-3005). Sensitization of BALB/c mice with ovalbumin induces a high level of ovalbumin-specific IgE in serum. Inhalation of ovalbumin in sensitized mice causes an immediate bronchoconstrictive response. Repeated inhalation of ovalbumin in sensitized animals induces nonspecific airway hyperresponsiveness in vivo, and infiltration of leukocytes in airway tissue.

Briefly, male BALB/c mice were actively sensitised by IP injection of 20 μg of ovalbumin in aluminium hydroxide adjuvant on days 0 and 14. Ten days after the last injection, mice were exposed to ovalbumin aerosols (1% OVA in saline), once per day for 3 Days (days 24, 25 and 26). The aerosol was generated with a nebulizer such as Medix 8001 (Sussex, UK). Animals were exposed for 30 minutes per aerosol challenge.

The antisense oligonucleotides were given to the mice during the challenge period. On days 17, 19, 21, 24 and 26, sensitised mice were dosed with 0.01, 1 or 100 μg/kg of ISIS 348592 (SEQ ID NO: 136)or ISIS 348574 (SEQ ID NO: 119)by aerosol administration.

The treatment groups were as follows:

| Group | Treatment (ASO) | Dose (μg/kg body weight) |
|---|---|---|
| 1 | ISIS 348592 (SEQ ID NO: 136) | 0.01 |
| 2 | ISIS 348592 (SEQ ID NO: 136) | 1 |
| 3 | ISIS 348592 (SEQ ID NO: 136) | 100 |
| 4 | ISIS 348574 (SEQ ID NO: 119) | 0.01 |
| 5 | ISIS 348574 (SEQ ID NO: 119) | 1 |
| 6 | ISIS 348574 (SEQ ID NO: 119) | 100 |
| 7 | Vehicle | |
| 8 | Naive | |

There were 10 animals in each treatment group and all animals were sacrificed on day 28. There were two control groups, one receiving the aerosol vehicle alone (Group 7) the other control group being a naive control (Group 8).

Airway responsiveness to methacholine was measured in vivo 48 hours after the last aerosol exposure using the airoverflow pressure method, in which bronchial resistance to inflation was measured. Baseline nebulized methacholine dose response curves were constructed at day 0 before antigen sensitization for all groups of animals. Pulmonary function was monitored using a Buxco BioSystem Plethysmograph (Buxco, Troy N.Y.) and expressed as enhanced pause (Penh) which correlates to measured airway resistance (Hamelmann et al., Am. J. Respir. Crit. Care Med., 1997, 156, 766-775).

Mice were anaesthetised by IP injection of urethan and placed on a heated blanket. The trachea was cannulated and a small polyethylene catheter placed in the jugular vein for intravenous administrations. Spontaneous breathing was suppressed by intravenous injection of tubocurarine chloride. When it stopped, the tracheal cannula was attached to a respiration pump. Airway responsiveness was measured at 48 hours after antigen challenge by measuring the airway response to methacholine at each dose. Post-challenge recordings were compared to baseline recordings for each group to generate a Penh stimulation index. The results are presented in FIGS. 1 to 4.

FIG. 1 plots the average Penh stimulation indexes in each group for increasing methacholine concentrations ((1)—♦—is 348592 (SEQ ID NO: 136) at 0.01 μg/kg; (2)—■—is 348592 (SEQ ID NO: 136) at 1 μg/kg; (3)—▲—is 348592 (SEQ ID NO: 136) at 100 μg/kg; (4)—x—is 348574 (SEQ ID NO: 119) at 0.01 μg/kg; (5)—*—is 348574 (SEQ ID NO: 119) at 1 μg/kg; (6)—●—is 348574 (SEQ ID NO: 119) at 100 μg/kg; (7)—|—is the vehicle; (8)—is the naive.

Using the JMP Statistical package to compare the entire curves, Tukey HSD shows that the vehicle group is different to all the other groups, that the naive group is similar to the groups of animals which received ASO ISIS 348574 (SEQ ID NO: 119) (at 0.01, 1 and 100 μg/kg) (i.e. groups 4 (—x—), 5 (—*—) and 6 (—○—)), and that the naive group is different to the groups of animals which received ASO ISIS 348592 (at 0.01, 1 and 100 μg/kg) (i.e. groups 1 (—♦—), 2 (—■—) and 3 (—▲—)). Student T analysis showed the same as Tukey HSD.

Figure 2:
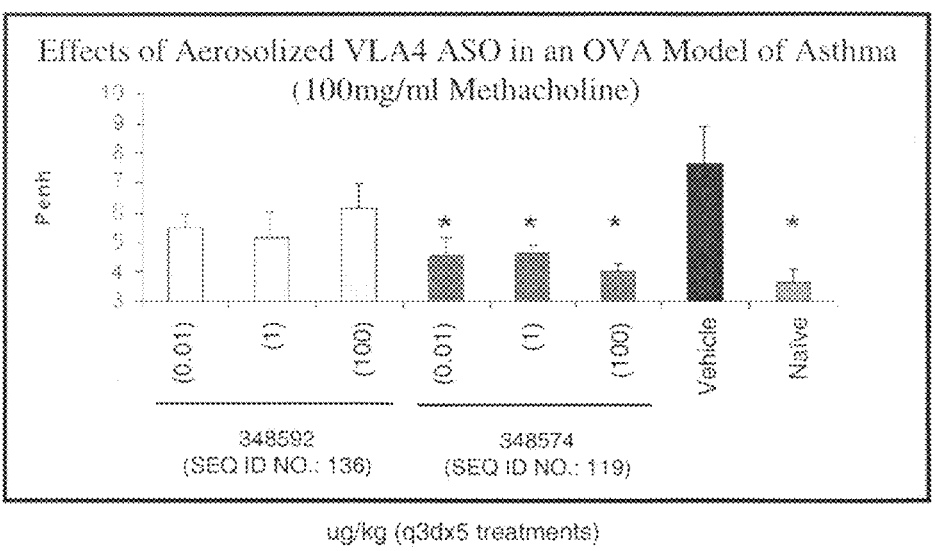
FIG. 2: Shows the effects of 0.01, 1 and 100 µg/kg doses of aerosolised integrin α4 ASOs (ISIS 348592 (SEQ ID NO: 136) or 348574 (SEQ ID NO: 119)) on Pen H at 100 mg/ml methacholine in an OVA model of asthma.
Figure 3:
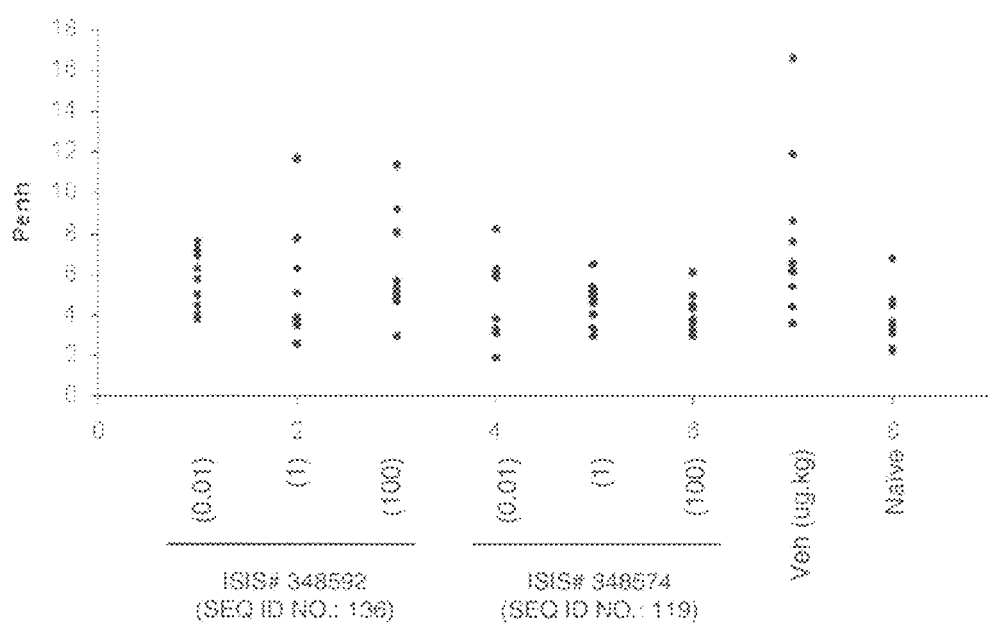
FIG. 3: Shows the effects of the 0.01, 1 and 100 µg/kg doses of aerosolised integrin α4 ASOs (ISIS 348592 (SEQ ID NO: 136) or 348574 (SEQ ID NO: 119)) on Pen H at 100 mg/ml methacholine on the individual mice from the study referred to in FIG. 2.
Figure 4:
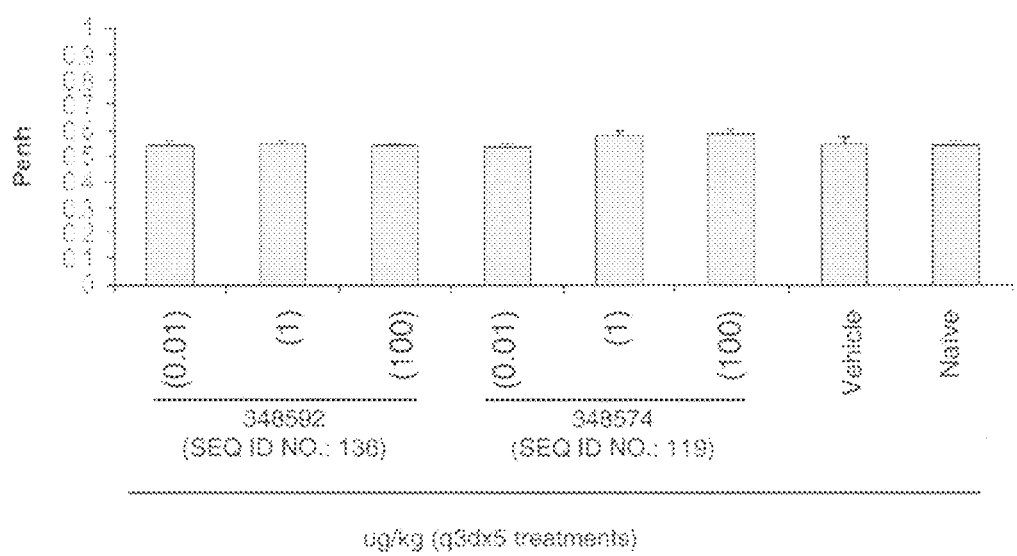
FIG. 4: Shows the effects of aerosolised integrin α4 ASOs (ISIS 348592 (SEQ ID NO: 119) or 348574 (SEQ ID NO: 119)) vs vehicle control on the baseline Pen H response in an OVA model model of asthma.

FIG. 2 is bar chart showing the Penh stimulation indexes for each group at a methacholine concentration of 100 mg/ml. Again, with respect to the ISIS 348574 (SEQ ID NO: 119) groups (4, 5 and 6), there is a significant reduction in Penh stimulation indexes ($P \leq 0.05$ vs the vehicle group). FIG. 3 shows the Penh stimulation indexes for each individual animal in each group at a methacholine concentration of 100 mg/ml. FIG. 4 shows the baseline figures for each treatment group.

These results clearly demonstrate that the ASOs inhibited the methacholine-induced allergic airway hyperresponsiveness, reducing the peak Penh index from approximately 7.5 (no oligo) to approximately 4.5 (ISIS 348574 (SEQ ID NO: 119) at 0.01 and 1 μg/kg), approximately 4 (ISIS 348574 at (SEQ ID NO: 119) 100 μg/kg), approximately 5.5 (ISIS 348592 (SEQ ID NO: 136) at 0.01 μg/kg), approximately 5.0 (ISIS 348592 (SEQ ID NO: 136) at 1 μg/kg) and approximately 6.25 (ISIS 348592 (SEQ ID NO: 136) at 100 μg/kg). This study is proof of the concept of integrin α4 antisense compound activity in a mouse model for asthma and demonstrates that a very low dose (e.g. 0.01 μg/kg) is highly effective at inhibiting AHR. It further demonstrates that aerosol administration appears to be a highly effect route of administration of the antisense compounds for the treatment of such respiratory conditions.

Bronchoalveolar lavage (BAL) was used to measure the cell infiltration of airway tissue. 48 hours after the last aerosol, mice were anaesthetised, tracheal cannulation performed and saline washes collected. Mice were lavaged five times with 1 ml aliquots of pyrogen-free saline. The cells derived from each lavage were pooled, washed with cold PBS and resuspended in 200 µl of cold PBS. Total numbers of cells were counted and categorized. The results are presented in FIGS. 5 to 8.

Figure 5:
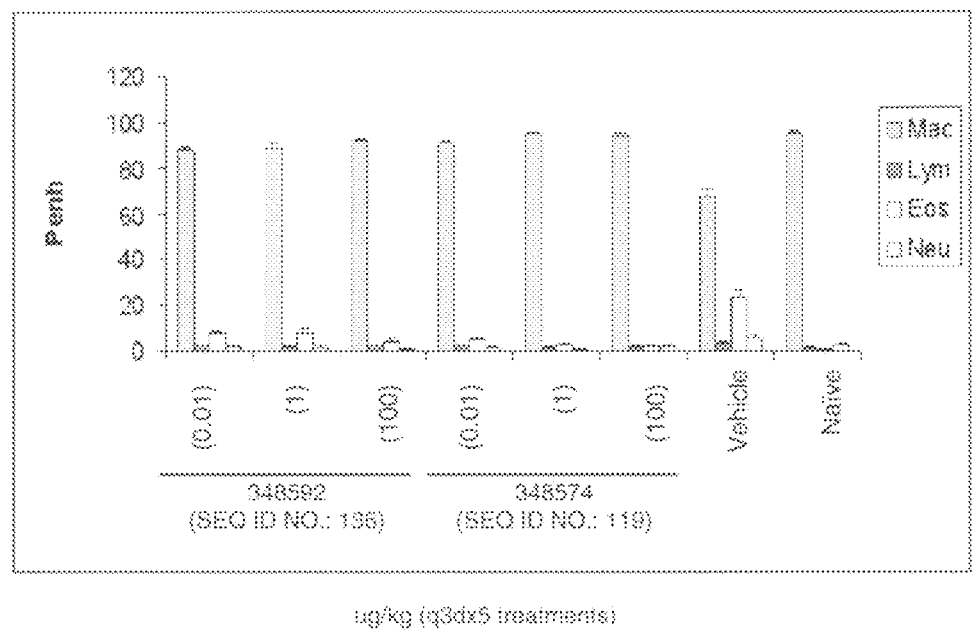
FIG. 5: Shows the effects of 0.01, 1 and 100 µg/kg doses of aerosolised integrin α4 ASOs (ISIS 348592 (SEQ ID NO: 136) or 348574 (SEQ ID NO: 119)) on BAL cell recruitment in an OVA model of asthma. It shows the percentage of cells (macrophages, lymphocytes, eosinophils and neutrophils) in the airway lung (bronchial airway lavage). In each set of 4 bars, from the left to right, the first bar is macrophages, the second bar is lymphocytes, the third bar is eosinophils and the fourth bar is neutrophils.

FIG. 5 is a bar chart plotting the average number of macrophage ("Mac"), lymphocyte ("Lym"), eosinophil ("Eos") and neutrophil ("Neu") cells as a percentage of the cells in the airway for each treatment group. A significant decrease in eosinophil recruitment was observed in all the groups treated with antisense compounds, Additionally, there also appeared to be a decrease in all the antisense treated groups of lymphocyte and neutrophil recruitment.

Figure 6:
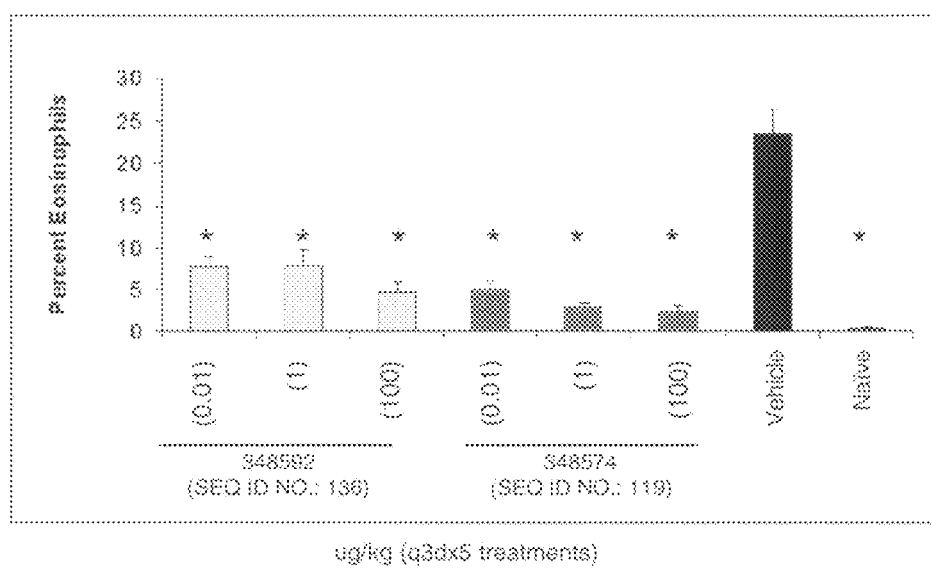
FIG. 6: Shows the effects of 0.01, 1 and 100 µg/kg doses of aerosolised integrin α4 ASOs (ISIS 348592 (SEQ ID NO: 136) or 348574 (SEQ ID NO: 119)) on eosinophil recruitment in an OVA model of asthma. It shows the percentage of eosinophils in the airway lung.
Figure 7:
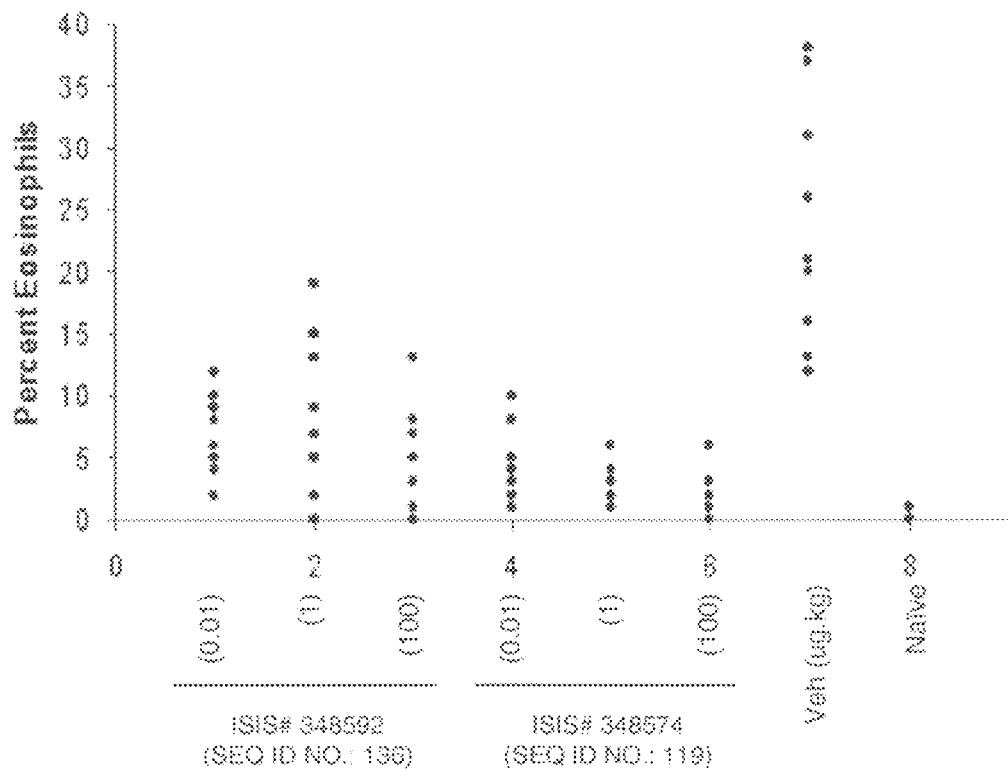
FIG. 7: Shows the effects of the 0.01, 1 and 100 µg/kg doses of aerosolised integrin α4 ASOs (ISIS 348592 (SEQ ID NO: 136) or 348574 (SEQ ID NO: 119)) on eosinophil recruitment in the airway lung in the individual mice for the study referred to in FIG. 6.

FIG. 6 is bar chart showing the average number of eosinophils for each group. For all the groups treated with ASOs (i.e. groups 1-3 treated with 0.01, 1 and 100 µg/kg ISIS 348592 (SEQ ID NO: 136), respectively, and groups 4-6 treated with 0.01, 1 and 100 µg/kg ISIS 348574 (SEQ ID NO: 119), respectively), there is a significant decrease in eosinophil recruitment (P≤0.05 vs the vehicle group). FIG. 7 shows the number of eosinophils for each individual animal in each group.

Figure 8A:
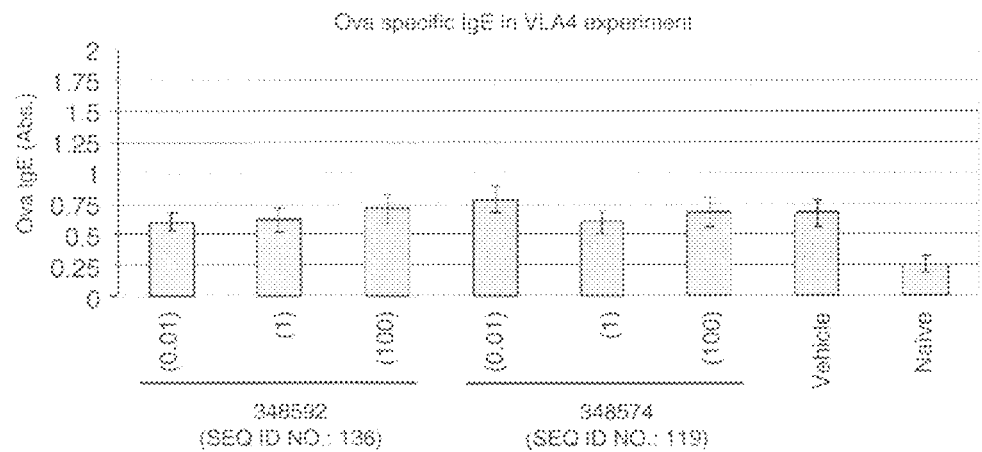
FIG. 8a: Shows the effects of 0.01, 1 and 100 µg/kg doses of aerosolised integrin α4 ASOs (ISIS 348592 (SEQ ID NO: 136) or 348574 (SEQ ID NO: 119)) on OVA IgE responses.
Figure 8B:
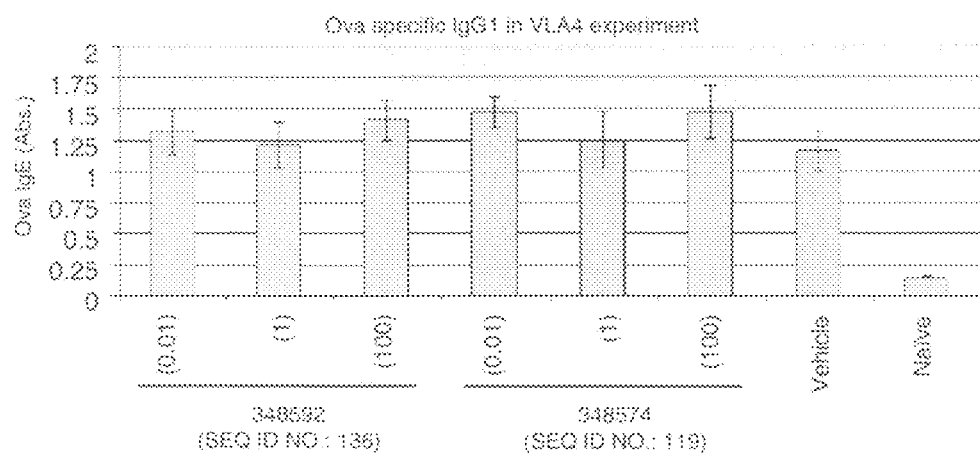
FIG. 8b: Shows the effects of 0.01, 1 and 100 µg/kg doses of aerosolised integrin α4 ASOs (ISIS 348592 (SEQ ID NO: 136) or 348574 (SEQ ID NO: 119)) on OVA IgG1 responses.

FIGS. 8a and 8b show the levels of ovalbumin-specific IgE and IgG1 for each of the treatment groups 1 to 8.

Example 2

In vivo Study on Ability of Aerosol Administered ASOs to Reduce the Number of Pas-positive Airways in Allergen Challenged Mice This study evaluated the ability of ISIS 348574 (SEQ ID NO: 119) to reduce the level of mucus produced in an in vivo murine model of allergic asthma and compared it with an 8 mismatch control ASO ISIS 358342(SEQ ID NO: 179). The level of mucus was assessed through staining with periodic acid-schiff (PAS) reagent.

Mice were sensitised, challenged and treated with ASOs exactly as described in study 1. The treatment groups were as follows:

| Group | Treatment (ASO) | Dose (µg/kg body weight) |
| --- | --- | --- |
| 1 | ISIS 348574 (SEQ ID NO: 119) | 0.01 |
| 2 | ISIS 348574 (SEQ ID NO: 119) | 1 |
| 3 | ISIS 348574 (SEQ ID NO: 119) | 100 |
| 4 | ISIS 358342 (SEQ ID NO: 179) | 0.01 |
| 5 | ISIS 358342 (SEQ ID NO: 179) | 1 |
| 6 | ISIS 358342 (SEQ ID NO: 179) | 100 |
| 7 | Vehicle | |
| 8 | Naive | |

There were 15 animals in each treatment group. There were two control groups, one receiving the aerosol vehicle alone (Group 7) the other control group being a naive control (Group 8). At day 27, five animals in each group underwent FACS. At day 28, the remaining 10 animals in each group where sacrificed.

Lungs were inflated and fixed in formalin, parasagittal sections were cut and mounted, slides were stained with PAS and images collected (x5) (two images per mouse). The vehicle and 1 µg/kg groups were compared. The results are presented in FIG. 9.

Figure 9:
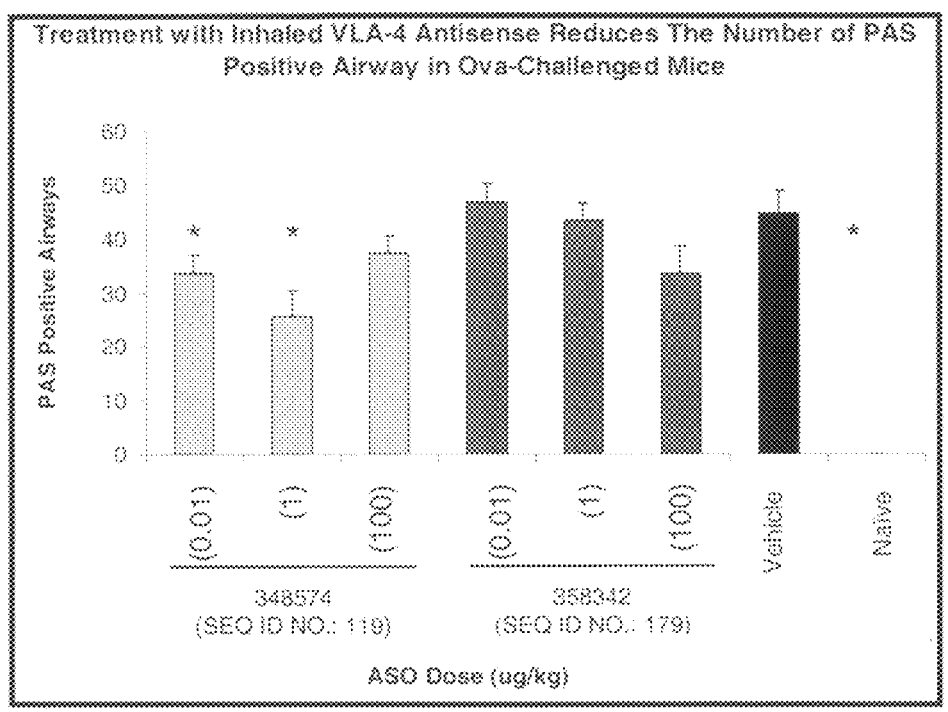
FIG. 9: Shows the effects of 0.01, 1 and 100 µg/kg dose of aerosolised integrin α4 ASO (ISIS 348574 (SEQ ID NO: 119)) versus control oligonucleotide ISIS 358342 (SEQ ID NO: 179) on the number of PAS positive airways in OVA model of asthma.
Figure 10:
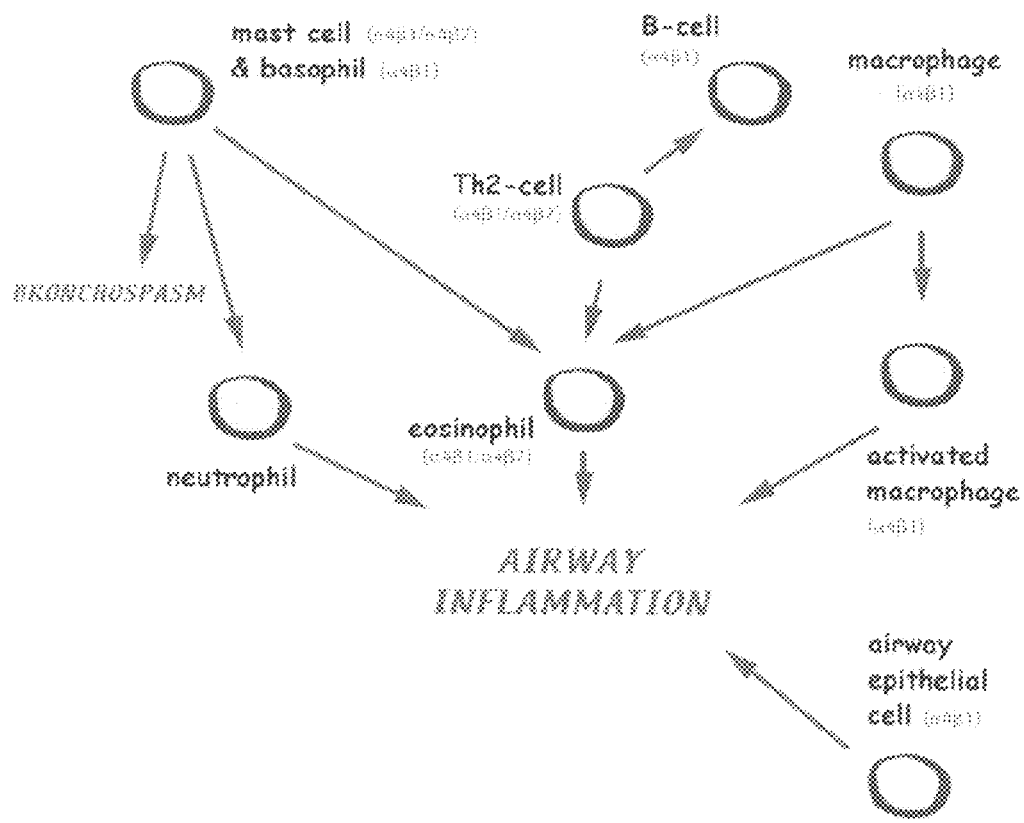
FIG. 10: Schematic representation of the possible cellular response involved in airway inflammation and the integrin alpha4 expression profile of the various cells.

FIG. 9 is a bar chart showing the average number of PAS positive airways for each treatment group. A clear decrease in PAS positive airways is observed in treatment groups 1-3, i.e. those groups which received ASO ISIS 348574 (SEQ ID NO: 119), which the decrease being significant at dose levels of 0.01 and 1 µg/kg (P≤0.05 vs the vehicle group). This indicates a reduction in airway mucus after antisense treatment.

Example 3

In vivo Study on the Target-mediated Pharmacological Activity of an Aerosol Administered ASO in a Mouse Model of Asthma E-cadherin positive cells are epithelial cells of which about 25% are mucuc-producing goblet cells. This study evaluated the ability of ISIS 348574 (SEQ ID NO: 119) to target integrin α4 production in E-cadherin positive cells and compared it with the 8 mismatch (MM) control ASO ISIS 358342 (SEQ ID NO: 179).

Mice were sensitised, challenged and treated with ASOs exactly as described in study 1. The treatment groups were as follows:

| Group | Treatment | Dose (µg/kg body weight) |
| --- | --- | --- |
| 1 | ISIS 348574 (ASO) (SEQ ID NO: 119) | 0.01 |
| 2 | ISIS 348574 (ASO) (SEQ ID NO: 119) | 1 |
| 3 | ISIS 358342 (MM) (SEQ ID NO: 179) | 0.01 |
| 4 | ISIS 358342 (MM) (SEQ ID NO: 179) | 1 |
| 5 | Vehicle | |
| 6 | Naive | |

There were 15 animals in each treatment group. There were two control groups, one receiving the aerosol vehicle alone (Group 5) the other control group being a naive control (Group 6). At day 27, five animals in each group underwent FACS. At day 28, the remaining 10 animals in each group where sacrificed. Lungs were recovered and digested with collagenase. Cell composition and VLA-4 protein expression in recovered lung cells was determined by immunostaining with specific monoclonal antibodies followed by flow cytometric analysis (FACS).

Figure 11:
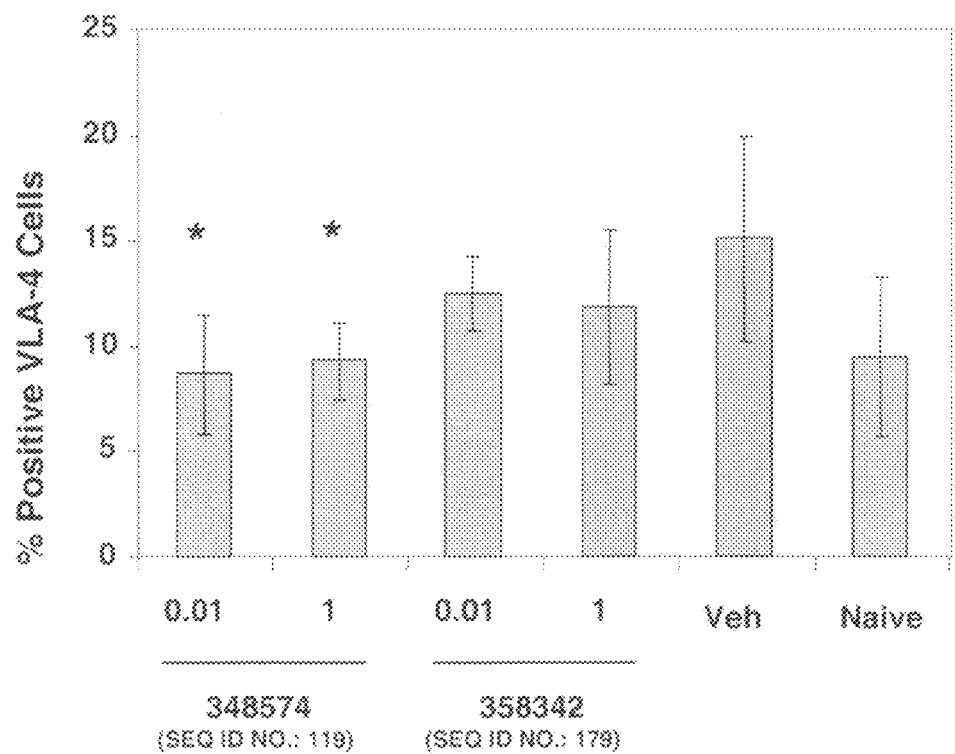
FIG. 11: Shows the effects of 0.01 and 1 µg/kg doses of an aerosolised integrin α4 ASO (ISIS 348574 (SEQ ID NO: 119)) and mismatch negative control oligonucleotide (ISIS 358342 (SEQ ID NO: 179)) on the percentage of E cadherin positive cells (epithelial cells) in the airway lung that also express integrin α4.

The cells were exposed to labelled antibodies to E-cadherin and integrin α4. The results are shown in FIG. 11. The E-cadherin positive cell population showed a statistically significant decrease in the percentage cells also positive for integrin α4 at both 0.01 and 1 µg/kg antisense dosages (* P<0.05 versus vehicle).

Thus, low doses of ASO appears to specifically reduce integrin α4 levels in the E cadherin positive cell population.

In summary, aerosol administration of integrin α4 ASO to ovalbumin-sensitised mice prior to local allergen challenge reduced the level of integrin α4 protein expressed on the surface of the lung cells, inhibited AHR (FIGS. 1-4), suppressed allergen-induced eosinophil and lymphocyte infiltration of the airways (FIGS. 5-7) and reduced the number of PAS positive airways (FIG. 9), this being indicative of a reduction in mucus. An 8 base pair-mismatch control oligonucleotide sequence was without effect.

The potential for integrin α4 to inhibit multiple processes that play important roles in inflammation suggests that integrin α4 antisense compounds, delivered at low doses, can be effective therapeutics for the treatment of respiratory conditions such as chronic asthma. Furthermore, our results demonstrate that topical, especially aerosol, delivery is a highly effective means of administration. Our results also confirm that integrin α4 plays a vital role in AHR and eosinophile recruitment to the airways in a mouse asthma model.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for the treatment and/or prophylaxis of an animal having a respiratory disease or condition associated with airway hyperresponsiveness, eosinophilia, neutrophilia, leukocytes or overproduction of mucus comprising topically administering to the respiratory system or airway of the animal an antisense compound targeted to a nucleic acid molecule encoding integrin α4, wherein the antisense compound is administered at a daily dosage level of from 0.01 to 100 μg per kg body weight of the animal.

2. The method of claim 1, in which the composition is to be administered no more than once daily.

3. The method of claim 1, in which the antisense compound is administered at a dose of no more than 5 μg per kg body weight of the individual animal.

4. The method of claim 1, in which the antisense compound is administered at a dose of no more than 1 μg per kg body weight of the individual animal.

5. The method of claim 1, in which the composition is topically administered via inhalation or insufflation.

6. The method of claim 1, in which the composition is to be administered via a route selected from the group consisting of: intrapulmonarily, intranasally and intratracheally.

7. The method of claim 6, in which the composition is administered via a device selected from the group consisting of: a metered dose inhaler (MDI), a nebuliser and a dry powder inhaler (DPI).

8. The method of claim 1, in which the disease or condition is selected from the group consisting of: asthma, cystic fibrosis, alpha-1 antitrypsin deficiency, chronic obstructive pulmonary disease chronic bronchitis and rhinitis.

9. The method according to claim 8, in which the disease or condition is asthma.

10. The method of claim 1, in which the antisense compound comprises an antisense oligonucleotide.

11. The method of claim 10, in which the antisense compound comprises an antisense oligonucleotide selected from the group consisting of: SEQ ID NOs. 81, 117, 120, 121, 122, 128, 130, 131, 132, 136, 137, 138, 141, 149, 150, 159, 160, 161, 167 and 168.

12. The method of claim 11, in which the antisense compound comprises an antisense oligonucleotide of SEQ ID NO. 81.

13. The method of claim 1, in which the antisense compound inhibits the expression of integrin α4 by at least 50%.

14. The method of claim 1, in which the antisense compound is administered at a dose of 100 μg per kg body weight of the individual animal.

* * * * *

SEQUENCE LISTING

```
<160> NUMBER OF SEQ ID NOS: 179

<210> SEQ ID NO 1
<211> LENGTH: 3567
<212> TYPE: DNA
<213> ORGANISM: Homo sapiens

<400> SEQUENCE: 1
cgccatcccg cgctctgcgg actgggaggc ccgggccagg acgcgagtct gcgcagccga      60
ggttccccag cgccccctgc agccgcgcgt aggcagagac ggagcccggc cctgcgcctc     120
cgcaccacgc ccgggacccc acccagcggc ccgtacccgc agaagcagcg cgagcacccg     180
aagctcccgg ctcggcggca gaaacgggga gtggggccgg gcgagtgcgc ggcatcccag     240
gccggcccga acgtccgccc gcggtgggcc gacttcccct cctcttccct ctctccttcc     300
tttagcccgc tggcgccgga cacgctgcgc ctcatctctt ggggcgttct tccccgttgg     360
ccaaccgtcg catcccgtgc aactttgggg tagtggccgc ttagtgttga atgttcccca     420
ccgagagcgc atggcttggg aagcgaggcg cgaacccggg ccccgaagcc gccgtccggg     480
agacggtgat gctgttgctg tgcctggggg tcccgaccgg ccgcccctac aacgtggaca     540
ctgagagcgc gctgctttac cagggccccc acaacacgct gttcggctac tcggtcgtgc     600
tgcacagcca cggggcgaac cgatggctcc tagtgggtgc gcccactgcc aactggctcg     660
ccaacgcttc agtgatcaat cccggggcga tttacagatg caggatcgga aagaatcccg     720
gccagacgtg cgaacagctc cagctgggta gccctaatgg agaaccttgt ggaaagactt     780
gtttggaaga gagagacaat cagtggttgg gggtcacact ttccagacag ccaggagaaa     840
atggatccat cgtgacttgt gggcatagat ggaaaaatat attttacata aagaatgaaa     900
ataagctccc cactggtggt tgctatggag tgcccccctga tttacgaaca gaactgagta     960
aaagaatagc tccgtgttat caagattatg tgaaaaaatt tggagaaaat tttgcatcat    1020
gtcaagctgg aatatccagt ttttacacaa aggatttaat tgtgatgggg gccccaggat    1080
catcttactg gactggctct cttttttgtct acaatataac tacaaataaa tacaaggctt    1140
ttttagacaa acaaaatcaa gtaaaattttg gaagttattt aggatattca gtcggagctg    1200
gtcattttcg gagccagcat actaccgaag tagtcggagg agctcctcaa catgagcaga    1260
ttggtaaggc atatatattc agcattgatg aaaaagaact aaatatctta catgaaatga    1320
aaggtaaaaa gcttggatcg tactttggag cttctgtctg tgctgtggac ctcaatgcag    1380
atggcttctc agatctgctc gtgggagcac ccatgcagag caccatcaga gaggaaggaa    1440
gagtgtttgt gtacatcaac tctggctcgg gagcagtaat gaatgcaatg gaaacaaacc    1500
tcgttggaag tgacaaatat gctgcaagat ttggggaatc tatagttaat cttggcgaca    1560
ttgacaatga tggctttgaa gatgttgcta tcggagctcc acaagaagat gacttgcaag    1620
gtgctattta tatttacaat ggccgtgcag atgggatctc gtcaaccttc tcacagagaa    1680
ttgaaggact tcagatcagc aaatcgttaa gtatgtttgg acagtctata tcaggacaaa    1740
ttgatgcaga taataatggc tatgtagatg tagcagttgg tgcttttcgg tctgattctg    1800
ctgtcttgct aaggacaaga cctgtagtaa ttgttgacgc ttctttaagc caccctgagt    1860
cagtaaatag aacgaaattt gactgtgttg aaaatggatg gccttctgtg tgcatagatc    1920
```

```
taacactttg tttctcatat aagggcaagg aagttccagg ttacattgtt ttgttttata      1980
acatgagttt ggatgtgaac agaaaggcag agtctccacc aagattctat ttctcttcta      2040
atggaacttc tgacgtgatt acaggaagca tacaggtgtc cagcagagaa gctaactgta      2100
gaacacatca agcatttatg cggaaagatg tgcgggacat cctcacccca attcagattg      2160
aagctgctta ccaccttggt cctcatgtca tcagtaaacg aagtacagag gaattcccac      2220
cacttcagcc aattcttcag cagaagaaag aaaaagacat aatgaaaaaa acaataaact      2280
ttgcaaggtt ttgtgcccat gaaaattgtt ctgctgattt acaggtttct gcaaagattg      2340 ggttttttgaa gccccatgaa aataaaacat atcttgctgt tgggagtatg aagacattga      2400
tgttgaatgt gtccttgttt aatgctggag atgatgcata tgaaacgact ctacatgtca      2460
aactacccgt gggtctttat ttcattaaga ttttagagct ggaagagaag caaataaact      2520
gtgaagtcac agataactct ggcgtggtac aacttgactg cagtattggc tatatatatg      2580
tagatcatct ctcaaggata gatattagct ttctcctgga tgtgagctca ctcagcagag      2640
cggaagagga cctcagtatc acagtgcatg ctacctgtga aaatgaagag gaaatggaca      2700
atctaaagca cagcagagtg actgtagcaa taccctttaaa atatgaggtt aagctgactg      2760
ttcatgggtt tgtaaaccca acttcatttg tgtatggatc aaatgatgaa aatgagcctg      2820
aaacgtgcat ggtggagaaa atgaacttaa cttttccatgt tatcaacact ggcaatagta      2880
tggctcccaa tgttagtgtg gaaataatgg taccaaattc ttttagcccc caaactgata      2940
agctgttcaa cattttggat gtccagacta ctactggaga atgccacttt gaaaattatc      3000 aaaagagtgtg tgcattagag cagcaaaaga gtgcaatgca gaccttgaaa ggcatagtcc      3060
agttcttgtc caagactgat aagaggctat tgtactgcat aaaagctgat ccacattgtt      3120
taaatttctt gtgtaatttt gggaaaatgg aaagtggaaa agaagccagt gttcatatcc      3180
aactggaagg ccggccatcc attttagaaa tggatgagac ttcagcactc aagtttgaaa      3240
taagagcaac aggttttcca gagccaaatc caagagtaat tgaactaaac aaggatgaga      3300
atgttgcgca tgttctactg gaaggactac atcatcaaag acccaaacgt tatttcacca      3360
tagtgattat ttcaagtagc ttgctacttg gacttattgt acttctgttg atctcatatg      3420
ttatgtggaa ggctggcttc tttaaaagac aatacaaatc tatcctacaa gaagaaaaca      3480
gaagagacag ttggagttat atcaacagta aaagcaatga tgattaagga cttctttcaa      3540
attgagagaa tggaaaacag cccgccc                                         3567

<210> SEQ ID NO 2
<211> LENGTH: 18
<212> TYPE: DNA
<213> ORGANISM: Artificial Sequence
<220> FEATURE:
<223> OTHER INFORMATION: antisense sequence

<400> SEQUENCE: 2
ctccgtctct gcctacgc                                                   18

<210> SEQ ID NO 3
<211> LENGTH: 18
<212> TYPE: DNA
<213> ORGANISM: Artificial sequence
<220> FEATURE:
<223> OTHER INFORMATION: antisense sequence

<400> SEQUENCE: 3
cgggtgctcg cgctgctt                                                   18
```

<210> SEQ ID NO 4
<211> LENGTH: 18
<212> TYPE: DNA
<213> ORGANISM: Artificial sequence
<220> FEATURE:
<223> OTHER INFORMATION: antisense sequence

<400> SEQUENCE: 4
cctgggatgc cgcgcact                                                 18

<210> SEQ ID NO 5
<211> LENGTH: 18
<212> TYPE: DNA
<213> ORGANISM: Artificial sequence
<220> FEATURE:
<223> OTHER INFORMATION: antisense sequence

<400> SEQUENCE: 5
atgaggcgca gcgtgtcc                                                 18

<210> SEQ ID NO 6
<211> LENGTH: 18
<212> TYPE: DNA
<213> ORGANISM: Artificial sequence
<220> FEATURE:
<223> OTHER INFORMATION: antisense sequence

<400> SEQUENCE: 6
caaagttgca cgggatgc                                                 18

<210> SEQ ID NO 7
<211> LENGTH: 18
<212> TYPE: DNA
<213> ORGANISM: Artificial sequence
<220> FEATURE:
<223> OTHER INFORMATION: antisense sequence

<400> SEQUENCE: 7
ggaacattca acactaag                                                 18

<210> SEQ ID NO 8
<211> LENGTH: 18
<212> TYPE: DNA
<213> ORGANISM: Artificial sequence
<220> FEATURE:
<223> OTHER INFORMATION: antisense sequence

<400> SEQUENCE: 8
cccgggttcg cgcctcgc                                                 18

<210> SEQ ID NO 9
<211> LENGTH: 18
<212> TYPE: DNA
<213> ORGANISM: Artificial sequence
<220> FEATURE:
<223> OTHER INFORMATION: antisense sequence

<400> SEQUENCE: 9
gcgcgctctc agtgtcca                                                 18

<210> SEQ ID NO 10
<211> LENGTH: 18
<212> TYPE: DNA
<213> ORGANISM: Artificial sequence
<220> FEATURE:

<223> OTHER INFORMATION: antisense sequence

<400> SEQUENCE: 10
gtggctgtgc agcacgac                                                    18

<210> SEQ ID NO 11
<211> LENGTH: 18
<212> TYPE: DNA
<213> ORGANISM: Artificial sequence
<220> FEATURE:
<223> OTHER INFORMATION: antisense sequence

<400> SEQUENCE: 11
actgaagcgt tggcgagc                                                    18

<210> SEQ ID NO 12
<211> LENGTH: 18
<212> TYPE: DNA
<213> ORGANISM: Artificial sequence
<220> FEATURE:
<223> OTHER INFORMATION: antisense sequence

<400> SEQUENCE: 12
gcacgtctgg ccgggatt                                                    18

<210> SEQ ID NO 13
<211> LENGTH: 18
<212> TYPE: DNA
<213> ORGANISM: Artificial sequence
<220> FEATURE:
<223> OTHER INFORMATION: antisense sequence

<400> SEQUENCE: 13
ccactgattg tctctctc                                                    18

<210> SEQ ID NO 14
<211> LENGTH: 18
<212> TYPE: DNA
<213> ORGANISM: Artificial sequence
<220> FEATURE:
<223> OTHER INFORMATION: antisense sequence

<400> SEQUENCE: 14
ggatccattt tctcctgg                                                    18

<210> SEQ ID NO 15
<211> LENGTH: 18
<212> TYPE: DNA
<213> ORGANISM: Artificial sequence
<220> FEATURE:
<223> OTHER INFORMATION: antisense sequence

<400> SEQUENCE: 15
gcttattttc attcttta                                                    18

<210> SEQ ID NO 16
<211> LENGTH: 18
<212> TYPE: DNA
<213> ORGANISM: Artificial Sequence
<220> FEATURE:
<223> OTHER INFORMATION: antisense sequence

<400> SEQUENCE: 16
ttcttttact cagttctg                                                    18

```
<210> SEQ ID NO 17
<211> LENGTH: 18
<212> TYPE: DNA
<213> ORGANISM: Artificial Sequence
<220> FEATURE:
<223> OTHER INFORMATION: antisense sequence

<400> SEQUENCE: 17
tcacataatc ttgataac                                                   18

<210> SEQ ID NO 18
<211> LENGTH: 18
<212> TYPE: DNA
<213> ORGANISM: Artificial Sequence
<220> FEATURE:
<223> OTHER INFORMATION: antisense sequence

<400> SEQUENCE: 18
cccatcacaa ttaaatcc                                                   18

<210> SEQ ID NO 19
<211> LENGTH: 18
<212> TYPE: DNA
<213> ORGANISM: Artificial Sequence
<220> FEATURE:
<223> OTHER INFORMATION: antisense sequence

<400> SEQUENCE: 19
ttatttgtag ttatattg                                                   18

<210> SEQ ID NO 20
<211> LENGTH: 18
<212> TYPE: DNA
<213> ORGANISM: Artificial Sequence
<220> FEATURE:
<223> OTHER INFORMATION: antisense sequence

<400> SEQUENCE: 20
cctaaataac ttccaaat                                                   18

<210> SEQ ID NO 21
<211> LENGTH: 18
<212> TYPE: DNA
<213> ORGANISM: Artificial Sequence
<220> FEATURE:
<223> OTHER INFORMATION: antisense sequence

<400> SEQUENCE: 21
gaaaatgacc agctccga                                                   18

<210> SEQ ID NO 22
<211> LENGTH: 18
<212> TYPE: DNA
<213> ORGANISM: Artificial Sequence
<220> FEATURE:
<223> OTHER INFORMATION: antisense sequence

<400> SEQUENCE: 22
tttcatgtaa gatattta                                                   18

<210> SEQ ID NO 23
<211> LENGTH: 18
<212> TYPE: DNA
<213> ORGANISM: Artificial Sequence
<220> FEATURE:
<223> OTHER INFORMATION: antisense sequence
```

```
<400> SEQUENCE: 23
ccacagcaca gacagaag                                                 18

<210> SEQ ID NO 24
<211> LENGTH: 18
<212> TYPE: DNA
<213> ORGANISM: Artificial Sequence
<220> FEATURE:
<223> OTHER INFORMATION: antisense sequence

<400> SEQUENCE: 24
tggtgctctg catgggtg                                                 18

<210> SEQ ID NO 25
<211> LENGTH: 18
<212> TYPE: DNA
<213> ORGANISM: Artificial Sequence
<220> FEATURE:
<223> OTHER INFORMATION: antisense sequence

<400> SEQUENCE: 25
tacacaaaca ctcttcct                                                 18

<210> SEQ ID NO 26
<211> LENGTH: 18
<212> TYPE: DNA
<213> ORGANISM: Artificial Sequence
<220> FEATURE:
<223> OTHER INFORMATION: antisense sequence

<400> SEQUENCE: 26
tttgtttcca ttgcattc                                                 18

<210> SEQ ID NO 27
<211> LENGTH: 18
<212> TYPE: DNA
<213> ORGANISM: Artificial Sequence
<220> FEATURE:
<223> OTHER INFORMATION: antisense sequence

<400> SEQUENCE: 27
tgcagcatat ttgtcact                                                 18

<210> SEQ ID NO 28
<211> LENGTH: 18
<212> TYPE: DNA
<213> ORGANISM: Artificial Sequence
<220> FEATURE:
<223> OTHER INFORMATION: antisense sequence

<400> SEQUENCE: 28
ttgtcaatgt cgccaaga                                                 18

<210> SEQ ID NO 29
<211> LENGTH: 18
<212> TYPE: DNA
<213> ORGANISM: Artificial Sequence
<220> FEATURE:
<223> OTHER INFORMATION: antisense sequence

<400> SEQUENCE: 29
tcatcttctt gtggagct                                                 18

<210> SEQ ID NO 30
<211> LENGTH: 18
```

```
<212> TYPE: DNA
<213> ORGANISM: Artificial Sequence
<220> FEATURE:
<223> OTHER INFORMATION: antisense sequence

<400> SEQUENCE: 30
ccatctgcac ggccattg                                                 18

<210> SEQ ID NO 31
<211> LENGTH: 18
<212> TYPE: DNA
<213> ORGANISM: Artificial Sequence
<220> FEATURE:
<223> OTHER INFORMATION: antisense sequence

<400> SEQUENCE: 31
gtccaaacat acttaacg                                                 18

<210> SEQ ID NO 32
<211> LENGTH: 18
<212> TYPE: DNA
<213> ORGANISM: Artificial Sequence
<220> FEATURE:
<223> OTHER INFORMATION: antisense sequence

<400> SEQUENCE: 32
tatctgcatc aatttgtc                                                 18

<210> SEQ ID NO 33
<211> LENGTH: 18
<212> TYPE: DNA
<213> ORGANISM: Artificial Sequence
<220> FEATURE:
<223> OTHER INFORMATION: antisense sequence

<400> SEQUENCE: 33
accgaaaagc accaactg                                                 18

<210> SEQ ID NO 34
<211> LENGTH: 18
<212> TYPE: DNA
<213> ORGANISM: Artificial Sequence
<220> FEATURE:
<223> OTHER INFORMATION: antisense sequence

<400> SEQUENCE: 34
cttgtcctta gcaagaca                                                 18

<210> SEQ ID NO 35
<211> LENGTH: 18
<212> TYPE: DNA
<213> ORGANISM: Artificial Sequence
<220> FEATURE:
<223> OTHER INFORMATION: antisense sequence

<400> SEQUENCE: 35
tcagggtggc ttaaagaa                                                 18

<210> SEQ ID NO 36
<211> LENGTH: 18
<212> TYPE: DNA
<213> ORGANISM: Artificial Sequence
<220> FEATURE:
<223> OTHER INFORMATION: antisense sequence

<400> SEQUENCE: 36
```

```
atccattttc aacacagt                                              18

<210> SEQ ID NO 37
<211> LENGTH: 18
<212> TYPE: DNA
<213> ORGANISM: Artificial Sequence
<220> FEATURE:
<223> OTHER INFORMATION: antisense sequence

<400> SEQUENCE: 37
gcccttatat gagaaaca                                              18

<210> SEQ ID NO 38
<211> LENGTH: 18
<212> TYPE: DNA
<213> ORGANISM: Artificial Sequence
<220> FEATURE:
<223> OTHER INFORMATION: antisense sequence

<400> SEQUENCE: 38
caatttgaaa gaagtcct                                              18

<210> SEQ ID NO 39
<211> LENGTH: 18
<212> TYPE: DNA
<213> ORGANISM: Artificial Sequence
<220> FEATURE:
<223> OTHER INFORMATION: antisense sequence

<400> SEQUENCE: 39
tccattctct caatttga                                              18

<210> SEQ ID NO 40
<211> LENGTH: 18
<212> TYPE: DNA
<213> ORGANISM: Artificial Sequence
<220> FEATURE:
<223> OTHER INFORMATION: antisense sequence

<400> SEQUENCE: 40
ggcgggctgt tttccatt                                              18

<210> SEQ ID NO 41
<211> LENGTH: 1300
<212> TYPE: DNA
<213> ORGANISM: Homo sapiens

<400> SEQUENCE: 41
ggcagggcac acctggattg cattagaatg agactcacta cccagttcag gtgtgttgcg      60
ttgtgggtct ccggcacatt tcagaggctg attaggaccc tgaccccaca ctgggggtta     120 caccccctaaa agcaggtgtg tcccgtggca actgagtggg tgcgtgaaaa gggggggatca   180 tcaattacca gctggagcaa tcgaatcggt taaatgtgaa tcaagtcaca gtgcttcctt     240
aacccaacct ctctgttggg gtcagccaca gcctaaaccg cctgccgttc agcctgagag     300
gctgctgcta gcctgctcac gcatgcagcc cgggctgcag aggaagtgtg gggaggaagg     360
aagtgggtat agaagggtgc tgagatgtgg gtcttgaaga gaatagccat aacgtctttg     420
tcactaaaat gttccccagg ggccttcggc gagtcttttt gtttggtttt tgttttttaa     480
tctgtggctc ttgataattt atctagtggt tgcctacacc tgaaaaacaa gacacagtgt     540
ttaactatca acgaaagaac tggacggctc ccgccgcag tcccactccc cgagtttgtg     600
gctggcattt gggccacgcc gggctgggcg gctcacagcg aggggcgcgc agtttggggt     660
```

-continued

```
cacacagctc cgcttctagg ccccaaccac cgttaaaagg ggaagcccgt gccccatcag    720
gtccgctctt gctgagccca gagccatccc gcgctctgcg ggctgggagg cccgggccag    780
acgcgagtcc tgcgcagccg aggttcccca gcgccccctg cagccgcgcg taggcagaga    840
cggagcccgg ccctgcgcct ccgcaccacg cccgggaccc cacccagcgg cccgtacccg    900
gagaagcagc gcgagcaccc gaagctcccg gctcggcggc agaaaccggg agtggggccg    960
ggcgagtgcg cggcatccca ggccggcccg aacgtccgcc cgcggtgggc cgacttcccc   1020
tcctcttccc tctctccttc ctttagcccg ctggcgccgg acacgctgcg cctcatctct   1080
tggggcgttc ttccccgttg gccaaccgtc gcatcccgtg caactttggg gtagtggccg   1140
cttagtgttg aatgttcccc accgagagcg catggcttgg gaagcgaggc gcgaacccgg   1200
gccccgaagc cgccgtccgg gagggccccc acaacacgct gttcggctac tcggtcgtgc   1260
tgcacagcca cggggcgaac cgatggtgag tagagttgga                         1300
```

<210> SEQ ID NO 42
<211> LENGTH: 20
<212> TYPE: DNA
<213> ORGANISM: Artificial Sequence
<220> FEATURE:
<223> OTHER INFORMATION: antisense sequence

<400> SEQUENCE: 42
tttagtgaca aagacgttat                                                 20

<210> SEQ ID NO 43
<211> LENGTH: 20
<212> TYPE: DNA
<213> ORGANISM: Artificial Sequence
<220> FEATURE:
<223> OTHER INFORMATION: antisense sequence

<400> SEQUENCE: 43
gaaggcccct ggggaacatt                                                 20

<210> SEQ ID NO 44
<211> LENGTH: 20
<212> TYPE: DNA
<213> ORGANISM: Artificial Sequence
<220> FEATURE:
<223> OTHER INFORMATION: antisense sequence

<400> SEQUENCE: 44
agacgttatg gctattctct                                                 20

<210> SEQ ID NO 45
<211> LENGTH: 20
<212> TYPE: DNA
<213> ORGANISM: Artificial Sequence
<220> FEATURE:
<223> OTHER INFORMATION: antisense sequence

<400> SEQUENCE: 45
ttgcccttat atgagaaaca                                                 20

<210> SEQ ID NO 46
<211> LENGTH: 20
<212> TYPE: DNA
<213> ORGANISM: Artificial Sequence
<220> FEATURE:
<223> OTHER INFORMATION: antisense sequence

```
<400> SEQUENCE: 46
cccaagccat gcgctctcgg                                                    20

<210> SEQ ID NO 47
<211> LENGTH: 20
<212> TYPE: DNA
<213> ORGANISM: Artificial Sequence
<220> FEATURE:
<223> OTHER INFORMATION: antisense sequence

<400> SEQUENCE: 47
ccgcagccat gcgctcttgg                                                    20

<210> SEQ ID NO 48
<211> LENGTH: 1771
<212> TYPE: DNA
<213> ORGANISM: Mus musculus

<400> SEQUENCE: 48
ccagcacttg cctcctgctc cagcgtgaaa agcagggaat ggaatatgga gtgtaagaca        60
taaattaaaa ataaaataaa attaaaaaaa aaaaagaaa agcagcacac aaggagtatg        120
ttcagcagag gcccatctcc tggcttaggt gtgctgtgac tctgatctct ggtggctttt       180
tagaagcctg ttatgacctt gtcttaggct gtgtctacac atctggtggt aggtatgtcc       240
tggggtaact gagtgtgtac atggggacta gttatgaaga agtgagcaag gggtggagtc       300
tgctaagtga ggcaagtcac agaatttcct tagcttgcct gggttttctg tgttaggcta       360
ttgcctggct tgctcatgcg tatagactct atttaagagg aagtgtatag agaggaagga      420
agcctgcata aaaggctgca ggcctgggag ttttgaagag actagccata tacttttgtc       480
accaaatgct ccaatagggc tggggcggga gggggggggg cagcagtttt ggcttcttgc      540
aaactgtgta atttctgtat gctacacagc acataagtga cagaggaagt tctggaaggt      600
tctccacagt cttagttccc aaattattgg ccactgggac tggccctgga ggccagtcac      660
ttggtgaagt cccgcaaggc atcaagcctt agccaacttt caaaagggaa tccctgatc       720 tgttttgtgt tccccaagg gttatttttg ctgggcccca gaagccagag ccactgtgtg       780
tgatgtctgc cagggtgtga gtccatgcaa cctaggtccc ctagcgcccc ctacagctgc      840
tgcggggcgg ggatggggat cgggttgggg agagggaggc caggctgtga gccactgcac      900
cacacccagg accccaccca gatcctagga gcacccggcc cctggctccg ggccacaga       960 aacgggcgt gggccagagc ctgaagcatc cctggccact acgatcgctc cgcctgtggc      1020
caccaattcc cctcctcttc tggcgtccct ctctccgccc ctgtcgcctg ccagcaccgg    1080
acacgctgct gcacttcatc tcttggggcg ctcttctctt tggccaaccg tcgcatcctg   1140
tgcaactctg gtcagtggcc gttttgtgtt gaatgttctc caccaagagc gcatggctgc   1200
ggaagcgagg tgcagaccga ggtcccgagg atcgccctc cgggaagcgg tgatgctgtt    1260
gttgtacttc ggggtgccaa ccgggcactc ctacaacctg acccggaga atgcactgct    1320 gtaccagggc ccctccggca cgctgttttgg ctactcggtg gtgctgcaca gccacgggtc   1380
gaagcgctgg tgagtgcgcc ctccccaaga ggcatgtcac agcgcctccg cctctgggat   1440
tccttgtatg aatcaaactt tccgccctcc tgggaggtca gagaaagacc tggcttcagc    1500
cagctgcctc actggagagc cttggaacta acttatcttg ggatggcagc ccccagggtg    1560
ctcctgagtc ctgggtctcc agtcatggga agaggaggtg ggtgccactt cccttgctga    1620
ccactgcaca gctgtcacaa gccaacacgg ggcagagtgg gtgggcagac tggttcacgt    1680
```

```
ctgagcgaac ttgcatggtt cttgctttag gctcatcgtg ggggctccca ctgccagctg    1740
gctctctaat gcctcagtgg tcaatcctgg g                                   1771

<210> SEQ ID NO 49
<211> LENGTH: 20
<212> TYPE: DNA
<213> ORGANISM: Artificial Sequence
<220> FEATURE:
<223> OTHER INFORMATION: antisense sequence

<400> SEQUENCE: 49
cacgccccgt ttctgtggcc                                                 20

<210> SEQ ID NO 50
<211> LENGTH: 20
<212> TYPE: DNA
<213> ORGANISM: Artificial Sequence
<220> FEATURE:
<223> OTHER INFORMATION: antisense sequence

<400> SEQUENCE: 50
ggatgcttca ggctctggcc                                                 20

<210> SEQ ID NO 51
<211> LENGTH: 20
<212> TYPE: DNA
<213> ORGANISM: Artificial Sequence
<220> FEATURE:
<223> OTHER INFORMATION: antisense sequence

<400> SEQUENCE: 51
ggagcgatcg tagtggccag                                                 20

<210> SEQ ID NO 52
<211> LENGTH: 20
<212> TYPE: DNA
<213> ORGANISM: Artificial Sequence
<220> FEATURE:
<223> OTHER INFORMATION: antisense sequence

<400> SEQUENCE: 52
ccggtgctgg caggcgacag                                                 20

<210> SEQ ID NO 53
<211> LENGTH: 20
<212> TYPE: DNA
<213> ORGANISM: Artificial Sequence
<220> FEATURE:
<223> OTHER INFORMATION: antisense sequence

<400> SEQUENCE: 53
gatgaagtgc agcagcgtgt                                                 20

<210> SEQ ID NO 54
<211> LENGTH: 20
<212> TYPE: DNA
<213> ORGANISM: Artificial Sequence
<220> FEATURE:
<223> OTHER INFORMATION: antisense sequence

<400> SEQUENCE: 54
ggccactgac cagagttgca                                                 20

<210> SEQ ID NO 55
```

```
<211> LENGTH: 20
<212> TYPE: DNA
<213> ORGANISM: Artificial Sequence
<220> FEATURE:
<223> OTHER INFORMATION: antisense sequence

<400> SEQUENCE: 55
cacctcgctt ccgcagccat                                              20

<210> SEQ ID NO 56
<211> LENGTH: 20
<212> TYPE: DNA
<213> ORGANISM: Artificial Sequence
<220> FEATURE:
<223> OTHER INFORMATION: control sequence

<400> SEQUENCE: 56
cggaccagta ccagggttac                                              20

<210> SEQ ID NO 57
<211> LENGTH: 20
<212> TYPE: DNA
<213> ORGANISM: Artificial Sequence
<220> FEATURE:
<223> OTHER INFORMATION: control sequence

<400> SEQUENCE: 57
gccgacaccc gttcgttcgg                                              20

<210> SEQ ID NO 58
<211> LENGTH: 20
<212> TYPE: DNA
<213> ORGANISM: Artificial Sequence
<220> FEATURE:
<223> OTHER INFORMATION: control sequence

<400> SEQUENCE: 58
acctcctcgc tcacgcgcta                                              20

<210> SEQ ID NO 59
<211> LENGTH: 20
<212> TYPE: DNA
<213> ORGANISM: Artificial Sequence
<220> FEATURE:
<223> OTHER INFORMATION: antisense sequence

<400> SEQUENCE: 59
cgcttccgca gccatgcgct                                              20

<210> SEQ ID NO 60
<211> LENGTH: 13
<212> TYPE: PRT
<213> ORGANISM: Artificial Sequence
<220> FEATURE:
<223> OTHER INFORMATION: synthesized peptide

<400> SEQUENCE: 60

His Ser Leu Gly Lys Trp Leu Gly His Pro Asp Lys Phe
 1               5                  10

<210> SEQ ID NO 61
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 61
agtccgcaga gcgcgggatg                                               20

<210> SEQ ID NO 62
<211> LENGTH: 20
<212> TYPE: DNA
<213> ORGANISM: Artificial Sequence
<220> FEATURE:
<223> OTHER INFORMATION: antisense sequence

<400> SEQUENCE: 62
agactcgcgt cctggcccgg                                               20

<210> SEQ ID NO 63
<211> LENGTH: 20
<212> TYPE: DNA
<213> ORGANISM: Artificial Sequence
<220> FEATURE:
<223> OTHER INFORMATION: antisense sequence

<400> SEQUENCE: 63
gtgcggaggc gcagggccgg                                               20

<210> SEQ ID NO 64
<211> LENGTH: 20
<212> TYPE: DNA
<213> ORGANISM: Artificial Sequence
<220> FEATURE:
<223> OTHER INFORMATION: antisense sequence

<400> SEQUENCE: 64
ccggtttctg ccgccgagcc                                               20

<210> SEQ ID NO 65
<211> LENGTH: 19
<212> TYPE: DNA
<213> ORGANISM: Artificial Sequence
<220> FEATURE:
<223> OTHER INFORMATION: antisense sequence

<400> SEQUENCE: 65
agcgacggtt ggccaacgg                                                19

<210> SEQ ID NO 66
<211> LENGTH: 20
<212> TYPE: DNA
<213> ORGANISM: Artificial Sequence
<220> FEATURE:
<223> OTHER INFORMATION: antisense sequence

<400> SEQUENCE: 66
cccagcacat cggctctcgg                                               20

<210> SEQ ID NO 67
<211> LENGTH: 20
<212> TYPE: DNA
<213> ORGANISM: Artificial Sequence
<220> FEATURE:
<223> OTHER INFORMATION: antisense sequence

<400> SEQUENCE: 67
cttcccaagc catgcgctct                                               20

<210> SEQ ID NO 68
<211> LENGTH: 20
```

```
<212> TYPE: DNA
<213> ORGANISM: Artificial Sequence
<220> FEATURE:
<223> OTHER INFORMATION: antisense sequence

<400> SEQUENCE: 68
tcgcttccca agccatgcgc                                                20

<210> SEQ ID NO 69
<211> LENGTH: 20
<212> TYPE: DNA
<213> ORGANISM: Artificial Sequence
<220> FEATURE:
<223> OTHER INFORMATION: antisense sequence

<400> SEQUENCE: 69
gcctcgcttc ccaagccatg                                                20

<210> SEQ ID NO 70
<211> LENGTH: 20
<212> TYPE: DNA
<213> ORGANISM: Artificial Sequence
<220> FEATURE:
<223> OTHER INFORMATION: antisense sequence

<400> SEQUENCE: 70
cgcgcctcgc ttcccaagcc                                                20

<210> SEQ ID NO 71
<211> LENGTH: 20
<212> TYPE: DNA
<213> ORGANISM: Artificial Sequence
<220> FEATURE:
<223> OTHER INFORMATION: antisense sequence

<400> SEQUENCE: 71
tccttgccct tatatgagaa                                                20

<210> SEQ ID NO 72
<211> LENGTH: 20
<212> TYPE: DNA
<213> ORGANISM: Artificial Sequence
<220> FEATURE:
<223> OTHER INFORMATION: antisense sequence

<400> SEQUENCE: 72
acttccttgc ccttatatga                                                20

<210> SEQ ID NO 73
<211> LENGTH: 20
<212> TYPE: DNA
<213> ORGANISM: Artificial Sequence
<220> FEATURE:
<223> OTHER INFORMATION: antisense sequence

<400> SEQUENCE: 73
agagttatct gtgacttcac                                                20

<210> SEQ ID NO 74
<211> LENGTH: 20
<212> TYPE: DNA
<213> ORGANISM: Artificial Sequence
<220> FEATURE:
<223> OTHER INFORMATION: antisense sequence

<400> SEQUENCE: 74
```
gatactgagg tcctcttccg                                          20

<210> SEQ ID NO 75
<211> LENGTH: 20
<212> TYPE: DNA
<213> ORGANISM: Artificial Sequence
<220> FEATURE:
<223> OTHER INFORMATION: antisense sequence

<400> SEQUENCE: 75
tgagatcaac agaagtacaa                                          20

<210> SEQ ID NO 76
<211> LENGTH: 20
<212> TYPE: DNA
<213> ORGANISM: Artificial Sequence
<220> FEATURE:
<223> OTHER INFORMATION: antisense sequence

<400> SEQUENCE: 76
ccagccttcc acataacata                                          20

<210> SEQ ID NO 77
<211> LENGTH: 20
<212> TYPE: DNA
<213> ORGANISM: Artificial Sequence
<220> FEATURE:
<223> OTHER INFORMATION: antisense sequence

<400> SEQUENCE: 77
aggatagatt tgtattgtct                                          20

<210> SEQ ID NO 78
<211> LENGTH: 20
<212> TYPE: DNA
<213> ORGANISM: Artificial Sequence
<220> FEATURE:
<223> OTHER INFORMATION: antisense sequence

<400> SEQUENCE: 78
gttgatataa ctccaactgt                                          20

<210> SEQ ID NO 79
<211> LENGTH: 20
<212> TYPE: DNA
<213> ORGANISM: Artificial Sequence
<220> FEATURE:
<223> OTHER INFORMATION: antisense sequence

<400> SEQUENCE: 79
taatcatcat tgcttttact                                          20

<210> SEQ ID NO 80
<211> LENGTH: 20
<212> TYPE: DNA
<213> ORGANISM: Artificial Sequence
<220> FEATURE:
<223> OTHER INFORMATION: antisense sequence

<400> SEQUENCE: 80
aagaagtcct taatcatcat                                          20

<210> SEQ ID NO 81
<211> LENGTH: 20
<212> TYPE: DNA
<213> ORGANISM: Artificial Sequence

```
<220> FEATURE:
<223> OTHER INFORMATION: antisense sequence

<400> SEQUENCE: 81
ctgagtctgt tttccattct                                          20

<210> SEQ ID NO 82
<211> LENGTH: 20
<212> TYPE: DNA
<213> ORGANISM: Artificial Sequence
<220> FEATURE:
<223> OTHER INFORMATION: antisense sequence

<400> SEQUENCE: 82
cttgtaaaca gtgtcttta                                           20

<210> SEQ ID NO 83
<211> LENGTH: 20
<212> TYPE: DNA
<213> ORGANISM: Artificial Sequence
<220> FEATURE:
<223> OTHER INFORMATION: antisense sequence

<400> SEQUENCE: 83
gagtaaaaga agtccaaaca                                          20

<210> SEQ ID NO 84
<211> LENGTH: 20
<212> TYPE: DNA
<213> ORGANISM: Artificial Sequence
<220> FEATURE:
<223> OTHER INFORMATION: antisense sequence

<400> SEQUENCE: 84
ccttgcatga agacataata                                          20

<210> SEQ ID NO 85
<211> LENGTH: 20
<212> TYPE: DNA
<213> ORGANISM: Artificial Sequence
<220> FEATURE:
<223> OTHER INFORMATION: antisense sequence

<400> SEQUENCE: 85
aagagtaatc attgctgaga                                          20

<210> SEQ ID NO 86
<211> LENGTH: 20
<212> TYPE: DNA
<213> ORGANISM: Artificial Sequence
<220> FEATURE:
<223> OTHER INFORMATION: antisense sequence

<400> SEQUENCE: 86
tctttggctg tattattacc                                          20

<210> SEQ ID NO 87
<211> LENGTH: 20
<212> TYPE: DNA
<213> ORGANISM: Artificial Sequence
<220> FEATURE:
<223> OTHER INFORMATION: antisense sequence

<400> SEQUENCE: 87
tgctttagtg tttctctacc                                          20
```

<210> SEQ ID NO 88
<211> LENGTH: 20
<212> TYPE: DNA
<213> ORGANISM: Artificial Sequence
<220> FEATURE:
<223> OTHER INFORMATION: antisense sequence

<400> SEQUENCE: 88
aagtctaaga cttctccagt                                               20

<210> SEQ ID NO 89
<211> LENGTH: 20
<212> TYPE: DNA
<213> ORGANISM: Artificial Sequence
<220> FEATURE:
<223> OTHER INFORMATION: antisense sequence

<400> SEQUENCE: 89
gaggcaagca catatggtaa                                               20

<210> SEQ ID NO 90
<211> LENGTH: 20
<212> TYPE: DNA
<213> ORGANISM: Artificial Sequence
<220> FEATURE:
<223> OTHER INFORMATION: antisense sequence

<400> SEQUENCE: 90
tgaaatgaac ctctgcccac                                               20

<210> SEQ ID NO 91
<211> LENGTH: 20
<212> TYPE: DNA
<213> ORGANISM: Artificial Sequence
<220> FEATURE:
<223> OTHER INFORMATION: antisense sequence

<400> SEQUENCE: 91
ttaaagtgat aatggtccac                                               20

<210> SEQ ID NO 92
<211> LENGTH: 20
<212> TYPE: DNA
<213> ORGANISM: Artificial Sequence
<220> FEATURE:
<223> OTHER INFORMATION: antisense sequence

<400> SEQUENCE: 92
ggaacacagc ccgtaggaaa                                               20

<210> SEQ ID NO 93
<211> LENGTH: 20
<212> TYPE: DNA
<213> ORGANISM: Artificial Sequence
<220> FEATURE:
<223> OTHER INFORMATION: antisense sequence

<400> SEQUENCE: 93
tttgccagtt tggcctataa                                               20

<210> SEQ ID NO 94
<211> LENGTH: 17
<212> TYPE: DNA
<213> ORGANISM: Artificial Sequence
<220> FEATURE:
<223> OTHER INFORMATION: antisense sequence

<400> SEQUENCE: 94
gacacgctgc gcctcat                                                17

<210> SEQ ID NO 95
<211> LENGTH: 22
<212> TYPE: DNA
<213> ORGANISM: Artificial Sequence
<220> FEATURE:
<223> OTHER INFORMATION: antisense sequence

<400> SEQUENCE: 95
attcaacact aagcggccac tg                                          22

<210> SEQ ID NO 96
<211> LENGTH: 22
<212> TYPE: DNA
<213> ORGANISM: Artificial Sequence
<220> FEATURE:
<223> OTHER INFORMATION: antisense sequence

<400> SEQUENCE: 96
ccaaccgtcg catcccgtgc aa                                          22

<210> SEQ ID NO 97
<211> LENGTH: 19
<212> TYPE: DNA
<213> ORGANISM: Artificial Sequence
<220> FEATURE:
<223> OTHER INFORMATION: antisense sequence

<400> SEQUENCE: 97
gaaggtgaag gtcggagtc                                              19

<210> SEQ ID NO 98
<211> LENGTH: 20
<212> TYPE: DNA
<213> ORGANISM: Artificial Sequence
<220> FEATURE:
<223> OTHER INFORMATION: antisense sequence

<400> SEQUENCE: 98
gaagatggtg atgggatttc                                             20

<210> SEQ ID NO 99
<211> LENGTH: 20
<212> TYPE: DNA
<213> ORGANISM: Artificial Sequence
<220> FEATURE:
<223> OTHER INFORMATION: antisense sequence

<400> SEQUENCE: 99
caagcttccc gttctcagcc                                             20

<210> SEQ ID NO 100
<211> LENGTH: 26
<212> TYPE: DNA
<213> ORGANISM: Artificial Sequence
<220> FEATURE:
<223> OTHER INFORMATION: Oligonucleotide

<400> SEQUENCE: 100
gaaaggtaaa aagcttggct catact                                      26

<210> SEQ ID NO 101

```
<211> LENGTH: 22
<212> TYPE: DNA
<213> ORGANISM: Artificial Sequence
<220> FEATURE:
<223> OTHER INFORMATION: Oligonucleotide

<400> SEQUENCE: 101
tctgagaagc catctgcatt ga                                              22

<210> SEQ ID NO 102
<211> LENGTH: 24
<212> TYPE: DNA
<213> ORGANISM: Artificial Sequence
<220> FEATURE:
<223> OTHER INFORMATION: Oligonucleotide probe

<400> SEQUENCE: 102
tggagcttct gtctgcgctg tgga                                            24

<210> SEQ ID NO 103
<211> LENGTH: 20
<212> TYPE: DNA
<213> ORGANISM: Artificial Sequence
<220> FEATURE:
<223> OTHER INFORMATION: Oligonucleotide

<400> SEQUENCE: 103
agagcttcag tgttttgctt                                                 20

<210> SEQ ID NO 104
<211> LENGTH: 20
<212> TYPE: DNA
<213> ORGANISM: Artificial Sequence
<220> FEATURE:
<223> OTHER INFORMATION: Oligonucleotide

<400> SEQUENCE: 104
tatatgtaca tacacacaag                                                 20

<210> SEQ ID NO 105
<211> LENGTH: 20
<212> TYPE: DNA
<213> ORGANISM: Artificial Sequence
<220> FEATURE:
<223> OTHER INFORMATION: Oligonucleotide

<400> SEQUENCE: 105
agtggcaccc acctcctctt                                                 20

<210> SEQ ID NO 106
<211> LENGTH: 20
<212> TYPE: DNA
<213> ORGANISM: Artificial Sequence
<220> FEATURE:
<223> OTHER INFORMATION: Oligonucleotide

<400> SEQUENCE: 106
tcaacctcac cttagcaaca                                                 20

<210> SEQ ID NO 107
<211> LENGTH: 20
<212> TYPE: DNA
<213> ORGANISM: Artificial Sequence
<220> FEATURE:
<223> OTHER INFORMATION: Oligonucleotide

<400> SEQUENCE: 107
```
cttgggatgc aattaaatgc                                          20

<210> SEQ ID NO 108
<211> LENGTH: 20
<212> TYPE: DNA
<213> ORGANISM: Artificial Sequence
<220> FEATURE:
<223> OTHER INFORMATION: Oligonucleotide

<400> SEQUENCE: 108
aaatgcttac ccttgagagg                                          20

<210> SEQ ID NO 109
<211> LENGTH: 20
<212> TYPE: DNA
<213> ORGANISM: Artificial Sequence
<220> FEATURE:
<223> OTHER INFORMATION: Oligonucleotide

<400> SEQUENCE: 109
tcatgcaata cttgaaaaga                                          20

<210> SEQ ID NO 110
<211> LENGTH: 20
<212> TYPE: DNA
<213> ORGANISM: Artificial Sequence
<220> FEATURE:
<223> OTHER INFORMATION: Oligonucleotide

<400> SEQUENCE: 110
ggccactgac cagagttgca                                          20

<210> SEQ ID NO 111
<211> LENGTH: 20
<212> TYPE: DNA
<213> ORGANISM: Artificial Sequence
<220> FEATURE:
<223> OTHER INFORMATION: Oligonucleotide

<400> SEQUENCE: 111
ccgcagccat gcgctcttgg                                          20

<210> SEQ ID NO 112
<211> LENGTH: 20
<212> TYPE: DNA
<213> ORGANISM: Artificial Sequence
<220> FEATURE:
<223> OTHER INFORMATION: Oligonucleotide

<400> SEQUENCE: 112
cgcttccgca gccatgcgct                                          20

<210> SEQ ID NO 113
<211> LENGTH: 20
<212> TYPE: DNA
<213> ORGANISM: Artificial Sequence
<220> FEATURE:
<223> OTHER INFORMATION: Oligonucleotide

<400> SEQUENCE: 113
cacctcgctt ccgcagccat                                          20

<210> SEQ ID NO 114
<211> LENGTH: 20
<212> TYPE: DNA

```
<213> ORGANISM: Artificial Sequence
<220> FEATURE:
<223> OTHER INFORMATION: Oligonucleotide

<400> SEQUENCE: 114
ccaggttgta ggagtgcccg                                        20

<210> SEQ ID NO 115
<211> LENGTH: 20
<212> TYPE: DNA
<213> ORGANISM: Artificial Sequence
<220> FEATURE:
<223> OTHER INFORMATION: Oligonucleotide

<400> SEQUENCE: 115
agtagccaaa cagcgtgccg                                        20

<210> SEQ ID NO 116
<211> LENGTH: 20
<212> TYPE: DNA
<213> ORGANISM: Artificial Sequence
<220> FEATURE:
<223> OTHER INFORMATION: Oligonucleotide

<400> SEQUENCE: 116
gtggctgtgc agcaccaccg                                        20

<210> SEQ ID NO 117
<211> LENGTH: 20
<212> TYPE: DNA
<213> ORGANISM: Artificial Sequence
<220> FEATURE:
<223> OTHER INFORMATION: Oligonucleotide

<400> SEQUENCE: 117
cccagctgga gctgttcgca                                        20

<210> SEQ ID NO 118
<211> LENGTH: 20
<212> TYPE: DNA
<213> ORGANISM: Artificial Sequence
<220> FEATURE:
<223> OTHER INFORMATION: Oligonucleotide

<400> SEQUENCE: 118
ggctacccag ctggagctgt                                        20

<210> SEQ ID NO 119
<211> LENGTH: 20
<212> TYPE: DNA
<213> ORGANISM: Artificial Sequence
<220> FEATURE:
<223> OTHER INFORMATION: Oligonucleotide

<400> SEQUENCE: 119 atattttcc acctgtgccc                                         20

<210> SEQ ID NO 120
<211> LENGTH: 20
<212> TYPE: DNA
<213> ORGANISM: Artificial Sequence
<220> FEATURE:
<223> OTHER INFORMATION: Oligonucleotide

<400> SEQUENCE: 120
gcaaaatttt ctccaaattt                                        20
```

<210> SEQ ID NO 121
<211> LENGTH: 20
<212> TYPE: DNA
<213> ORGANISM: Artificial Sequence
<220> FEATURE:
<223> OTHER INFORMATION: Oligonucleotide

<400> SEQUENCE: 121
atgatgcaaa attttctcca                                          20

<210> SEQ ID NO 122
<211> LENGTH: 20
<212> TYPE: DNA
<213> ORGANISM: Artificial Sequence
<220> FEATURE:
<223> OTHER INFORMATION: Oligonucleotide

<400> SEQUENCE: 122
ccagcttgac atgatgcaaa                                          20

<210> SEQ ID NO 123
<211> LENGTH: 20
<212> TYPE: DNA
<213> ORGANISM: Artificial Sequence
<220> FEATURE:
<223> OTHER INFORMATION: Oligonucleotide

<400> SEQUENCE: 123
atattccagc ttgacatgat                                          20

<210> SEQ ID NO 124
<211> LENGTH: 20
<212> TYPE: DNA
<213> ORGANISM: Artificial Sequence
<220> FEATURE:
<223> OTHER INFORMATION: Oligonucleotide

<400> SEQUENCE: 124
gcccccatca caattaaatc                                          20

<210> SEQ ID NO 125
<211> LENGTH: 20
<212> TYPE: DNA
<213> ORGANISM: Artificial Sequence
<220> FEATURE:
<223> OTHER INFORMATION: Oligonucleotide

<400> SEQUENCE: 125
gtagttatat tgtagacaaa                                          20

<210> SEQ ID NO 126
<211> LENGTH: 20
<212> TYPE: DNA
<213> ORGANISM: Artificial Sequence
<220> FEATURE:
<223> OTHER INFORMATION: Oligonucleotide

<400> SEQUENCE: 126
actgagtagc ctaagtagct                                          20

<210> SEQ ID NO 127
<211> LENGTH: 20
<212> TYPE: DNA
<213> ORGANISM: Artificial Sequence
<220> FEATURE:

<223> OTHER INFORMATION: Oligonucleotide

<400> SEQUENCE: 127
ctatctgttc gtgttgaggg                                               20

<210> SEQ ID NO 128
<211> LENGTH: 20
<212> TYPE: DNA
<213> ORGANISM: Artificial Sequence
<220> FEATURE:
<223> OTHER INFORMATION: Oligonucleotide

<400> SEQUENCE: 128
ccaagctttt tacctttcat                                               20

<210> SEQ ID NO 129
<211> LENGTH: 20
<212> TYPE: DNA
<213> ORGANISM: Artificial Sequence
<220> FEATURE:
<223> OTHER INFORMATION: Oligonucleotide

<400> SEQUENCE: 129
cagacagaag ctccaaagta                                               20

<210> SEQ ID NO 130
<211> LENGTH: 20
<212> TYPE: DNA
<213> ORGANISM: Artificial Sequence
<220> FEATURE:
<223> OTHER INFORMATION: Oligonucleotide

<400> SEQUENCE: 130
ccatctgcat tgaggtccac                                               20

<210> SEQ ID NO 131
<211> LENGTH: 20
<212> TYPE: DNA
<213> ORGANISM: Artificial Sequence
<220> FEATURE:
<223> OTHER INFORMATION: Oligonucleotide

<400> SEQUENCE: 131
agaagccatc tgcattgagg                                               20

<210> SEQ ID NO 132
<211> LENGTH: 20
<212> TYPE: DNA
<213> ORGANISM: Artificial Sequence
<220> FEATURE:
<223> OTHER INFORMATION: Oligonucleotide

<400> SEQUENCE: 132
atctgagaag ccatctgcat                                               20

<210> SEQ ID NO 133
<211> LENGTH: 20
<212> TYPE: DNA
<213> ORGANISM: Artificial Sequence
<220> FEATURE:
<223> OTHER INFORMATION: Oligonucleotide

<400> SEQUENCE: 133
ctgatggtgc tctgcatggg                                               20

```
<210> SEQ ID NO 134
<211> LENGTH: 20
<212> TYPE: DNA
<213> ORGANISM: Artificial Sequence
<220> FEATURE:
<223> OTHER INFORMATION: Oligonucleotide

<400> SEQUENCE: 134
ccatgccaga gttgatgtac                                              20

<210> SEQ ID NO 135
<211> LENGTH: 20
<212> TYPE: DNA
<213> ORGANISM: Artificial Sequence
<220> FEATURE:
<223> OTHER INFORMATION: Oligonucleotide

<400> SEQUENCE: 135
catttcaacc atcacagctc                                              20

<210> SEQ ID NO 136
<211> LENGTH: 20
<212> TYPE: DNA
<213> ORGANISM: Artificial Sequence
<220> FEATURE:
<223> OTHER INFORMATION: Oligonucleotide

<400> SEQUENCE: 136
gcagcatatt tgtcacttcc                                              20

<210> SEQ ID NO 137
<211> LENGTH: 20
<212> TYPE: DNA
<213> ORGANISM: Artificial Sequence
<220> FEATURE:
<223> OTHER INFORMATION: Oligonucleotide

<400> SEQUENCE: 137
atcttgcagc atatttgtca                                              20

<210> SEQ ID NO 138
<211> LENGTH: 20
<212> TYPE: DNA
<213> ORGANISM: Artificial Sequence
<220> FEATURE:
<223> OTHER INFORMATION: Oligonucleotide

<400> SEQUENCE: 138
cccaaatctt gcagcatatt                                              20

<210> SEQ ID NO 139
<211> LENGTH: 20
<212> TYPE: DNA
<213> ORGANISM: Artificial Sequence
<220> FEATURE:
<223> OTHER INFORMATION: Oligonucleotide

<400> SEQUENCE: 139
ttgtcaatgt cgccaagatt                                              20

<210> SEQ ID NO 140
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 140
ccattgtaaa tgtagacagc                                              20

<210> SEQ ID NO 141
<211> LENGTH: 20
<212> TYPE: DNA
<213> ORGANISM: Artificial Sequence
<220> FEATURE:
<223> OTHER INFORMATION: Oligonucleotide

<400> SEQUENCE: 141
gtccttcaat tctctgtgag                                              20

<210> SEQ ID NO 142
<211> LENGTH: 20
<212> TYPE: DNA
<213> ORGANISM: Artificial Sequence
<220> FEATURE:
<223> OTHER INFORMATION: Oligonucleotide

<400> SEQUENCE: 142
tctgcatcaa tttgtcctga                                              20

<210> SEQ ID NO 143
<211> LENGTH: 20
<212> TYPE: DNA
<213> ORGANISM: Artificial Sequence
<220> FEATURE:
<223> OTHER INFORMATION: Oligonucleotide

<400> SEQUENCE: 143
catatccatt gttgtctgca                                              20

<210> SEQ ID NO 144
<211> LENGTH: 20
<212> TYPE: DNA
<213> ORGANISM: Artificial Sequence
<220> FEATURE:
<223> OTHER INFORMATION: Oligonucleotide

<400> SEQUENCE: 144
tccttagcaa cactgcagaa                                              20

<210> SEQ ID NO 145
<211> LENGTH: 20
<212> TYPE: DNA
<213> ORGANISM: Artificial Sequence
<220> FEATURE:
<223> OTHER INFORMATION: Oligonucleotide

<400> SEQUENCE: 145
gatgcttcaa caatcactac                                              20

<210> SEQ ID NO 146
<211> LENGTH: 20
<212> TYPE: DNA
<213> ORGANISM: Artificial Sequence
<220> FEATURE:
<223> OTHER INFORMATION: Oligonucleotide

<400> SEQUENCE: 146
atggcttaaa gatgcttcaa                                              20

<210> SEQ ID NO 147
<211> LENGTH: 20
```

```
<212> TYPE: DNA
<213> ORGANISM: Artificial Sequence
<220> FEATURE:
<223> OTHER INFORMATION: Oligonucleotide

<400> SEQUENCE: 147
tagcctggga cctctttgcc                                               20

<210> SEQ ID NO 148
<211> LENGTH: 20
<212> TYPE: DNA
<213> ORGANISM: Artificial Sequence
<220> FEATURE:
<223> OTHER INFORMATION: Oligonucleotide

<400> SEQUENCE: 148
caaaacgatg tagcctggga                                               20

<210> SEQ ID NO 149
<211> LENGTH: 20
<212> TYPE: DNA
<213> ORGANISM: Artificial Sequence
<220> FEATURE:
<223> OTHER INFORMATION: Oligonucleotide

<400> SEQUENCE: 149
cctgtaatca cgtcagaagt                                               20

<210> SEQ ID NO 150
<211> LENGTH: 20
<212> TYPE: DNA
<213> ORGANISM: Artificial Sequence
<220> FEATURE:
<223> OTHER INFORMATION: Oligonucleotide

<400> SEQUENCE: 150
tgcttcctgt aatcacgtca                                               20

<210> SEQ ID NO 151
<211> LENGTH: 20
<212> TYPE: DNA
<213> ORGANISM: Artificial Sequence
<220> FEATURE:
<223> OTHER INFORMATION: Oligonucleotide

<400> SEQUENCE: 151
ccactgcttg aaactcgtat                                               20

<210> SEQ ID NO 152
<211> LENGTH: 20
<212> TYPE: DNA
<213> ORGANISM: Artificial Sequence
<220> FEATURE:
<223> OTHER INFORMATION: Oligonucleotide

<400> SEQUENCE: 152
ggtgtgtcct acatttctct                                               20

<210> SEQ ID NO 153
<211> LENGTH: 20
<212> TYPE: DNA
<213> ORGANISM: Artificial Sequence
<220> FEATURE:
<223> OTHER INFORMATION: Oligonucleotide

<400> SEQUENCE: 153
```
gtctttccgc atgaatgcct                                                    20

<210> SEQ ID NO 154
<211> LENGTH: 20
<212> TYPE: DNA
<213> ORGANISM: Artificial Sequence
<220> FEATURE:
<223> OTHER INFORMATION: Oligonucleotide

<400> SEQUENCE: 154
ccaaggtggt atgtggcctc                                                    20

<210> SEQ ID NO 155
<211> LENGTH: 20
<212> TYPE: DNA
<213> ORGANISM: Artificial Sequence
<220> FEATURE:
<223> OTHER INFORMATION: Oligonucleotide

<400> SEQUENCE: 155
cacatgatgc ccaaggtggt                                                    20

<210> SEQ ID NO 156
<211> LENGTH: 19
<212> TYPE: DNA
<213> ORGANISM: Artificial Sequence
<220> FEATURE:
<223> OTHER INFORMATION: Oligonucleotide

<400> SEQUENCE: 156
gtttgtgatc acatgatgc                                                     19

<210> SEQ ID NO 157
<211> LENGTH: 20
<212> TYPE: DNA
<213> ORGANISM: Artificial Sequence
<220> FEATURE:
<223> OTHER INFORMATION: Oligonucleotide

<400> SEQUENCE: 157
caaaaccttg caaagtttat                                                    20

<210> SEQ ID NO 158
<211> LENGTH: 20
<212> TYPE: DNA
<213> ORGANISM: Artificial Sequence
<220> FEATURE:
<223> OTHER INFORMATION: Oligonucleotide

<400> SEQUENCE: 158
acatccagga gaaagctaat                                                    20

<210> SEQ ID NO 159
<211> LENGTH: 20
<212> TYPE: DNA
<213> ORGANISM: Artificial Sequence
<220> FEATURE:
<223> OTHER INFORMATION: Oligonucleotide

<400> SEQUENCE: 159
agctcacatc caggagaaag                                                    20

<210> SEQ ID NO 160
<211> LENGTH: 20
<212> TYPE: DNA
<213> ORGANISM: Artificial Sequence

```
<220> FEATURE:
<223> OTHER INFORMATION: Oligonucleotide

<400> SEQUENCE: 160
gagtgagctc acatccagga                                               20

<210> SEQ ID NO 161
<211> LENGTH: 20
<212> TYPE: DNA
<213> ORGANISM: Artificial Sequence
<220> FEATURE:
<223> OTHER INFORMATION: Oligonucleotide

<400> SEQUENCE: 161
ctgctgagtg agctcacatc                                               20

<210> SEQ ID NO 162
<211> LENGTH: 20
<212> TYPE: DNA
<213> ORGANISM: Artificial Sequence
<220> FEATURE:
<223> OTHER INFORMATION: Oligonucleotide

<400> SEQUENCE: 162
gttcacaagc ccatgaacag                                               20

<210> SEQ ID NO 163
<211> LENGTH: 20
<212> TYPE: DNA
<213> ORGANISM: Artificial Sequence
<220> FEATURE:
<223> OTHER INFORMATION: Oligonucleotide

<400> SEQUENCE: 163
tacacaaatg aagtttgggtt                                              20

<210> SEQ ID NO 164
<211> LENGTH: 20
<212> TYPE: DNA
<213> ORGANISM: Artificial Sequence
<220> FEATURE:
<223> OTHER INFORMATION: Oligonucleotide

<400> SEQUENCE: 164
atccatacac aaatgaagtt                                               20

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide

<400> SEQUENCE: 165
agaatttggt accattattt                                               20

<210> SEQ ID NO 166
<211> LENGTH: 20
<212> TYPE: DNA
<213> ORGANISM: Artificial Sequence
<220> FEATURE:
<223> OTHER INFORMATION: Oligonucleotide

<400> SEQUENCE: 166
tcatgcaata caggagtctc                                               20
```

```
<210> SEQ ID NO 167
<211> LENGTH: 20
<212> TYPE: DNA
<213> ORGANISM: Artificial Sequence
<220> FEATURE:
<223> OTHER INFORMATION: Oligonucleotide

<400> SEQUENCE: 167
cgtttgggtc tttgatgatg                                              20

<210> SEQ ID NO 168
<211> LENGTH: 20
<212> TYPE: DNA
<213> ORGANISM: Artificial Sequence
<220> FEATURE:
<223> OTHER INFORMATION: Oligonucleotide

<400> SEQUENCE: 168
ataagtccaa gtagcaagct                                              20

<210> SEQ ID NO 169
<211> LENGTH: 20
<212> TYPE: DNA
<213> ORGANISM: Artificial Sequence
<220> FEATURE:
<223> OTHER INFORMATION: Oligonucleotide

<400> SEQUENCE: 169
gtacaataag tccaagtagc                                              20

<210> SEQ ID NO 170
<211> LENGTH: 20
<212> TYPE: DNA
<213> ORGANISM: Artificial Sequence
<220> FEATURE:
<223> OTHER INFORMATION: Oligonucleotide

<400> SEQUENCE: 170
tcttgtagga tagatttgta                                              20

<210> SEQ ID NO 171
<211> LENGTH: 20
<212> TYPE: DNA
<213> ORGANISM: Artificial Sequence
<220> FEATURE:
<223> OTHER INFORMATION: Oligonucleotide

<400> SEQUENCE: 171
tagaagtctt cagtcatcat                                              20

<210> SEQ ID NO 172
<211> LENGTH: 19
<212> TYPE: DNA
<213> ORGANISM: Artificial Sequence
<220> FEATURE:
<223> OTHER INFORMATION: Oligonucleotide

<400> SEQUENCE: 172 gattccctg cactaagag                                                19

<210> SEQ ID NO 173
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 173
aagccacctt tgggtagctt                                                   20

<210> SEQ ID NO 174
<211> LENGTH: 20
<212> TYPE: DNA
<213> ORGANISM: Artificial Sequence
<220> FEATURE:
<223> OTHER INFORMATION: Oligonucleotide

<400> SEQUENCE: 174
gacggttggc caaagagaag                                                   20

<210> SEQ ID NO 175
<211> LENGTH: 20
<212> TYPE: DNA
<213> ORGANISM: Artificial Sequence
<220> FEATURE:
<223> OTHER INFORMATION: Oligonucleotide

<400> SEQUENCE: 175
cacgatgagc ctcctcttcc                                                   20

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide

<400> SEQUENCE: 176
cacacatgca tgattatatt                                                   20

<210> SEQ ID NO 177
<211> LENGTH: 20
<212> TYPE: DNA
<213> ORGANISM: Artificial Sequence
<220> FEATURE:
<223> OTHER INFORMATION: Oligonucleotide

<400> SEQUENCE: 177
gccccaaagg agatgtgata                                                   20

<210> SEQ ID NO 178
<211> LENGTH: 20
<212> TYPE: DNA
<213> ORGANISM: Artificial Sequence
<220> FEATURE:
<223> OTHER INFORMATION: Oligonucleotide

<400> SEQUENCE: 178
cgaggcgagc atttaccagc                                                   20

<210> SEQ ID NO 179
<211> LENGTH: 20
<212> TYPE: DNA
<213> ORGANISM: Artificial Sequence
<220> FEATURE:
<223> OTHER INFORMATION: Oligonucleotide

<400> SEQUENCE: 179
acagtgtacc tccttttctc                                                   20
```